United States Patent
Gokaraju et al.

(10) Patent No.: US 9,427,425 B2
(45) Date of Patent: Aug. 30, 2016

(54) EXTRACTS, FRACTIONS AND COMPOSITIONS COMPRISING ACETOGENINS AND THEIR APPLICATIONS

(75) Inventors: Ganga Raju Gokaraju, Vijayawada (IN); Rama Raju Gokaraju, Vijayawada (IN); Venkata Kanaka Ranga Raju Gokaraju, Vijayawada (IN); Trimurtulu Golakoti, Vijayawada (IN); Krishanu Sengupta, Vijayawada (IN); Kiran Bhupathiraju, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 261 days.

(21) Appl. No.: 13/450,124

(22) Filed: Apr. 18, 2012

(65) Prior Publication Data

US 2012/0201884 A1 Aug. 9, 2012

Related U.S. Application Data

(63) Continuation of application No. PCT/IN2010/000686, filed on Oct. 19, 2010.

(30) Foreign Application Priority Data

Oct. 19, 2009 (IN) .......................... 2526/CHE/2009

(51) Int. Cl.
| | |
|---|---|
| *A61K 31/365* | (2006.01) |
| *A61K 36/324* | (2006.01) |
| *A61K 36/61* | (2006.01) |
| *A61K 36/9066* | (2006.01) |
| *A61K 31/7008* | (2006.01) |
| *A61K 9/22* | (2006.01) |
| *A61P 3/00* | (2006.01) |
| *A61P 3/04* | (2006.01) |
| *A61P 3/10* | (2006.01) |
| *A61P 9/10* | (2006.01) |
| *A61P 9/12* | (2006.01) |
| *A61P 7/00* | (2006.01) |
| *A61K 36/185* | (2006.01) |

(52) U.S. Cl.
CPC ........... *A61K 31/365* (2013.01); *A61K 36/185* (2013.01)

(58) Field of Classification Search
None
See application file for complete search history.

(56) References Cited

U.S. PATENT DOCUMENTS

| 5,536,848 | A * | 7/1996 | McLaughlin et al. ........ 549/320 |
| 5,897,879 | A * | 4/1999 | Friedman et al. ............ 424/486 |
| 6,242,483 | B1 * | 6/2001 | McLaughlin et al. ........ 514/473 |
| 6,991,818 | B2 | 1/2006 | Shankaram et al. |
| 2003/0050336 | A1 * | 3/2003 | Shankaram et al. .......... 514/473 |
| 2005/0158355 | A1 * | 7/2005 | Yamashita .................... 424/410 |
| 2007/0218041 | A1 | 9/2007 | Lu et al. |
| 2008/0138367 | A1 | 6/2008 | Vromen |
| 2009/0029894 | A1 | 1/2009 | Okamoto et al. |
| 2009/0285864 | A1 * | 11/2009 | Godin .......................... 424/400 |

FOREIGN PATENT DOCUMENTS

| CN | 1477102 A | 2/2004 |
| IN | 2759/DEL/2006 A | 5/2008 |
| WO | WO 2007143631 A2 * | 12/2007 |
| WO | WO 2008125928 A2 * | 10/2008 |
| WO | 2009/030257 A | 3/2009 |
| WO | WO 2009030257 A1 * | 3/2009 |
| WO | 2011048617 | 4/2011 |

OTHER PUBLICATIONS

R.D. Leek, A.L. Harris, and C.E. Lewis. Cytokine networks in solid human tumors: regulation of angiogenesis. Journal of Leukocyte Biology vol. 56, Oct. 1994, pp. 423-435.*
Jean Yves Reginster, Rita Deroisy, Lucio C Rovati, Richard L Lee, Eric Lejeune, Olivier Bruyere, Giampaolo Giacovelli, Yves Henrotin, Jane E Dacre, Christiane Gossett. Long-term effects of glucosamine sulphate on osteoarthritis progression: a randomised, placebo-controlled clinical trial. Lancet 2001; 357: 251-56.*
Remco van Horssen, Timo L. M. ten Hagen, Alexander M. M. Eggermont. TNF-Alpha in Cancer Treatment: Molecular Insights, Antitumor Effects, and Clinical Utility. The Oncologist 2006, 11:397-408.*
Fernandes JC, Marte-Pelletier J, and Pelletier JP. The role of cytokines in osteoarthritis pathophysiology. Biorheology 2002; 39(1-2):237-246.*
Huachen Wei, Ronald Bowen, Qiuyin Cai, Stephen Barnes, Yan Wang. Antioxidant and Antipromotional Effects of the Soybean Isoflavone Genistein. Exp Biol Med (Maywood) Jan. 1995 vol. 208 No. 1 124-130. Abstract included.*
Koppaka V. Rao, Sunil K. Chattopadhyay, and G. Chandrasekhara Reddy. Flavonoids with Mosquito Larval Toxicity. J. Agric. Food Chem. 1990, 38, 1427-1430.*
Mahendra Sahai, et al. Annonaceous Acetogeoins from the Seeds of Annona squamosa. Adjacent Bis-tetrahydrofuranic Acetogenins. Chem. Pharm. Bull. 42(6) 1163-1174 (1994).*
Robert E King and Joseph D Schwartz, "Oral Solid Dosage Forms", Chapter 90, in Remington's Pharmaceutical Sciences, 17th Edition, edited by Alfonso Gennaro, 1985, pp. 1625 and 1629.*

(Continued)

*Primary Examiner* — Isaac Shomer
*Assistant Examiner* — Michael P Cohen
(74) *Attorney, Agent, or Firm* — Kramer Amado P.C.

(57) ABSTRACT

The current disclosure discloses acetogenin(s), extract(s)/fraction(s) standardized to acetogenin(s) comprising terminal α,β-unsaturated-γ-methyl-γ-lactone moiety derived from *Annona squamosa* or their compositions for prevention, treatment, inhibition or controlling inflammation and immune related diseases or disorders mediated through cytokines/chemokines or other biomarkers. The disclosure further discloses said *Annona squamosa* derived acetogenin(s), extract(s)/fraction(s) or their compositions for prevention, treatment, inhibition or controlling metabolic diseases/disorders.

19 Claims, 8 Drawing Sheets

(56) References Cited

OTHER PUBLICATIONS

Yu-Liang Yang, Kuo-Feng Hua, Pei-Hsuan Chuang, Shih-Hsiung Wu, Kuen-Yuh Wu, Fang-Rong Chang, and Yang-Chang Wu. New Cyclic Peptides from the Seeds of *Annona squamosa* L. and Their Anti-inflammatory Activities. J. Agric. Food Chem. 2008, 56, 386-392.*

Yang et al., New Cyclic Peptides from the Seeds of *Annona squamosa* L. and Theft Anti-inflammatory Activities. Journal Agricultural and Food Chemistry, 2008, vol. 56, No. 2, pp. 386-392.

International Search Report for PCT/IN2010/000686 dated May 2, 2011.

Feras Q. Alali, et al., Annonaceous Acetogenins: Recent Progress, J. Nat. Prod. 1999, 62, 504-540.

A.C. de Q. Pinto, Annona: Annona cherimola, A. muricata, A. reticulata, A. senegalensis and A. squamosa, Field Manual for Extension Workers and Farmers, University of Southampton, Southampton, UK. SCUC (2006).

Chavan et al., Analgesic and anti-inflammatory activity of Caryophyllene oxide from *Annona squamosa* L. bark. Phytomedicine 17 (2010) 149-151.

Junya Intaranongpai et al., Anti-head Lice Effect of Annona Squamosa Seeds. Southeast Asian J. Trop. Med. Public Health, 2006, vol. 37 No. 3 May 2006, pp. 532-535.

Mohamed Saleem TS et al., Hepatoprotective activity of Annona squamosa Linn. on experimental animal model International Journal of Applied Research in Natural Products. vol. 1 (3), pp. 1-7, Sep./Oct. 2008.

"International Search Report for PCT/IN2012/000313 dated Dec. 10, 2012".

Fitzpatrick, et al., "Double-Blind, half-Face Study Comparing Topical Vitamin C and Vehicle for Rejuventation of Photodamage.", Dermatol Surg 2002; 28; 231-236.

\* cited by examiner

EXTRACTS, FRACTIONS AND COMPOSITIONS COMPRISING ACETOGENINS AND THEIR APPLICATIONS

CROSS-REFERENCE TO RELATED APPLICATIONS

This application is a continuation in part of international application number PCT/IN2010/000686, filed 19 Oct. 2010 and published as WO 2011/048617, entitled "Extracts, Fractions and Compositions Comprising Acetogenins and Their Applications."

FIELD OF INVENTION

The current disclosure relates to acetogenins, extracts/fractions standardized to acetogenin(s) comprising terminal $\alpha,\beta$-unsaturated-$\gamma$-methyl-$\gamma$-lactone moiety derived from *Annona squamosa* for prevention, treatment, inhibition or controlling inflammation and/or immune related diseases mediated through cytokines/chemokines or other diagnostic/biomarkers. The invention further relates to extracts/fractions standardized to acetogenin(s) for the prevention, treatment, inhibition or controlling metabolic diseases/disorders.

BACKGROUND ART

*Annona squamosa* also known as Custard apple, Sugar-apple or Sweetsop, belongs to Annonaceae family and native to the tropical Americas. *Annona squamosa* is a shrub or small tree up to 6 m height. Custard apple is an edible fruit with white pulp that contains many black shiny seeds in it. It is commonly found in deciduous forests and also being cultivated in many parts of India. Pulp of the fruit is eaten fresh or converted into juice or shake. Fruits are normally eaten fresh. Its exact native range is unknown due to extensive cultivation, but thought to be in the Caribbean; the species was described from Jamaica.

Some of the phytochemistry of *Annona squamosa* is as follows. The volatile constituents of *Annona squamosa* L. bark were identified from the essential oil obtained by steam distillation. Six major components were identified as 1H-Cycloprop(e)azulene (3.46%), germacrene D (11.44%), bisabolene (4.48%), caryophyllene oxide (29.38%), bisabolene epoxide (3.64%) and kaur-16-ene (19.13%) were identified by studied by GC/MS.

Eleven annonaceous acetogenins compounds were isolated and identified as squamocenin, annotemoyin-2, reticulatain-2, squamocin-I, squamocin-B, squamocin, motrilin, squamostatin-D, squamostatin-E, cherimolin-1 and cherimolin-2 from the ethyl alcohol extract of *A. squamosa* L seeds.

Annonaceous acetogenins are a well-established class of natural compounds that have been isolated from plants in the Annonaceae family. Tetrahydrofuranic acetogenins are a prominent class among them [Feras, Q. A., et. al., *J. Nat. Prod.*, 1999, 62: 504-540]. It has been reported that various members of this class of compounds exhibit significant bioactivities. Acetogenins are $C_{35}$-$C_{39}$ compounds that typically contain two long hydrocarbon chains, one of which connects a terminal 2,4-disubstituted-$\gamma$-lactone to a variable number of tetrahydrofuran (THF) rings. The hydrocarbon chains contain a number of oxygenated moieties which can be hydroxyls, acetoxyls and/or ketones. Recently, single-ring acetogenins containing double bonds, epoxide compounds which lack THF rings and a compound lacking both epoxides and THF rings have been reported. These compounds support the proposed polyketide origin of the Annonaceous acetogenins.

Leaves of *Annona squamosa* were found to have mosquito insecticide properties and used for treating sleeping sickness. The crushed seeds were found to have insecticidal properties against fruit flies and lice. The fruit pulp contains vitamin C and is good for teeth, bones, skin and muscle. The flowers have been used to treat eye inflammation. Paste of seed powder is used to treat head lice and used in cancer treatment. The bark extract is used to treat skin diseases and control intestinal worms. The root extract is used to treat cancerous tumors. [A. C. de Q. Pinto, Field Manual for extension workers and farmers, Practical manual no. 5, 2006].

Some of the pharmacological activities of *Annona squamosa* are summarized below:

Cyclosquamosin D isolated from the seeds of *Annona squamosa* showed anti-inflammatory activity by inhibiting the production of pro-inflammatory cytokines within lipopolysaccharide and Pam3Cys-stimulated J774A.1 macrophages. [Yang, Y. L., et al., *J Agric Food Chem.* 2008, 56: 386-92].

Some of the active compounds isolated from *Annona squamosa* seed showed anti-head lice effect. [Junya Intaranongpai et al., Southeast Asian J. Trop. Med. Public Health, 2006, 37: pages]. Roots of *Annona squamosa* are known for the management of constipation. The hepatoprotective activity [Mohamed Saleem T S et al., *International Journal of Applied Research in Natural Products*, 2008, 1: 1-7.] was also reported for *Annona squamosa*.

Reactive oxygen species (ROS) and granule proteases produced by neutrophils contribute to the pathogenesis of inflammatory diseases. An ent-kurane compound 16-beta,17-dihydroxy-ent-kauran-19-oic acid isolated from the stems of *Annona squamosa* exhibited potent immunomodulating effects in leukocytes and anti-inflammatory activity through the inhibition of the generation of superoxide anion, the formation of ROS, and the release of elastase in formyl-L-methionyl-L-leucyl-L-phenylalanine (FMLP)-activated human neutrophils.

In another research study, the Caryophyllene oxide isolated from *Annona squamosa* at the doses of 12.5 and 25 mg/kg body wt. showed significant central as well as peripheral analgesic activity, along with anti-inflammatory activity. [Chavan, M. J., et al., *Phytomedicine.* 2009].

The anti-inflammatory activity of *Annona squamosa* was reported earlier in an Indian Patent application 2756/DEL/2006. The application describes a process of preparing an extract of *Annona squamosa* comprising the active compounds 16-Hydroxyoctadeca-9(Z or E), 12 (Z or E), 14(Z or E)-trienoic acid and 13-Hydroxy-9Z-11E-15E-octadecatrienoic acid and its use for the treatment of cancer, diabetes and related complications including inflammatory conditions such as AIDS, asthma, arthritis, bronchitis, chronic obstructive pulmonary disease (COPD), psoriasis, allergic rhinitis, shock, atopic dermatitis, Crohn's disease, adult respiratory distress syndrome (ARDS), eosinophilic granuloma, allergic conjunctivitis, osteoarthritis or ulcerative colitis. The trienoic acid compounds were attributed to be responsible for the activity.

Chinese patent application CN1477102 relates to sugar apple plant extract with the action of resisting diabetes, its application and preparation method. The raw material is extracted from branch, leaf, trunk, bark, root, seed and fruit skin of *Annona squamosa* plant. The acetogenin compounds can be made into various dosage forms for curing diabetes, and its preparation method can adopt one or several processes of solvent extraction process, resin adsorption process, supercritical CO2 extraction process and conventional drying process.

U.S. Pat. No. 6,242,483 relates to the isolation of three new mono-tetrahydrofuran ring acetogenins from the bark of *Annona squamosa*. Each of these compounds bears a carbonyl group at the C-9 position and two hydroxyls that flank the tetrahydrofuran ring. These compounds exhibit selective cytotoxic activity against certain specific human tumor cells.

SUMMARY OF THE INVENTION

In various embodiments, the current disclosure provides extract(s) or fraction(s) containing acetogenin(s) comprising terminal α,β-unsaturated-γ-methyl-γ-lactone moiety derived from *Annona squamosa* for prevention, treatment, inhibition or controlling inflammation and/or immune related diseases mediated through cytokines/chemokines or other biomarkers.

Various embodiments disclosed herein provide extracts of *Annona squamosa*, comprising from 0.01% to 30% by weight, preferably from 0.1% to 10% by weight, more preferably from 0.1% to 5% by weight, of at least one compound selected from the group consisting of acetogenins, said acetogenins each comprising a terminal α,β-unsaturated-γ-methyl-γ-lactone moiety of structure (a) and an optionally hydroxylated hydrocarbon chain, said hydrocarbon chain being interrupted by at least one bivalent group selected from the group consisting of a tetrahydrofuran group of structure (b) and an epoxy group of structure (c):

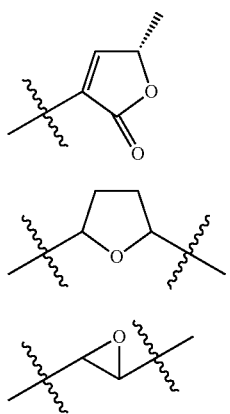

Some embodiments provide extracts of *Annona squamosa*, comprising from 0.01% to 30% by weight, preferably from 0.1% to 10% by weight, more preferably from 0.1% to 5% by weight, of at least one compound selected from the group consisting of acetogenins, wherein said acetogenins have a structure of formula:

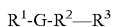

R$^1$-G-R$^2$—R$^3$ wherein R$^3$ is a terminal α,β-unsaturated-γ-methyl-γ-lactone moiety of structure (a) above; G is a group of formulas G$^1$-(L-G$^2$)$_q$, wherein G$^1$ and G$^2$ are independently selected from the group consisting of the tetrahydrofuran group of structure (b) above and the epoxy group of structure (c) above; q is 0, 1, or 2; and L is a direct bond or an optionally hydroxylated hydrocarbon linking group having from 2 to 4 carbon atoms; R$^1$ is an optionally hydroxylated linear hydrocarbon group having 8 to 12 carbon atoms, wherein R$^1$ contains from 0 to 2 double bonds; and R$^2$ is an optionally hydroxylated divalent linear hydrocarbon group having 8 to 13 carbon atoms, wherein R$^2$ contains from 0 to 2 double bonds. In certain embodiments, G is selected from the group consisting of:

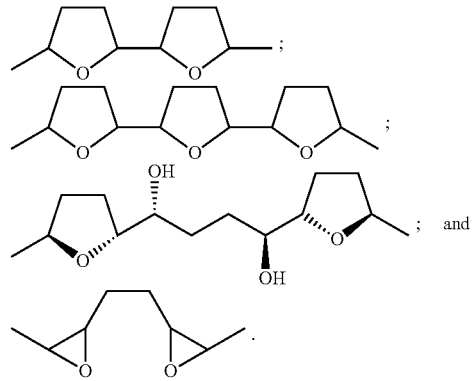

Some embodiments provide extracts of *Annona squamosa*, comprising from 0.01% to 30% by weight, preferably from 0.1% to 10% by weight, more preferably from 0.1% to 5% by weight, of at least one compound selected from the group consisting of compound 1, compound 2, compound 3, compound 4, compound 5, compound 6, compound 7, compound 8, compound 9, compound 10, compound 11, and mixtures thereof, where the structures of compounds 1 through 11 are presented in FIGS. 2A and 2B.

Various embodiments disclosed herein relate to herbal compositions comprising an extract of *Annona squamosa*, comprising from 0.01% to 50% by weight, preferably from 0.01% to 30% by weight, more preferably from 0.1% to 10% by weight, still more preferably from 0.1% to 5% by weight, of at least one acetogenins comprising a terminal α,β-unsaturated-γ-methyl-γ-lactone moiety of structure (a) and an optionally hydroxylated hydrocarbon chain, said hydrocarbon chain being interrupted by at least one bivalent group selected from the group consisting of a tetrahydrofuran group of structure (b) and an epoxy group of structure (c), in combination with at least one of:

at least one component selected from the group consisting of vitamins, amino acids, minerals, and mixtures thereof; and at least one pharmaceutically acceptable inactive ingredient selected from the group consisting of excipients, vehicles, carriers, diluents or mixtures thereof.

In various embodiments, the herbal compositions further comprise at least one extract or phytochemical having a health benefit, said health benefit being selected from the group consisting of anti-inflammatory activity, anti-arthritic activity, anti-diabetic activity, anti-hyperglycemic activity, hypolipidemic activity, anti-obesity activity, anti-hypertensive activity, anti-platelet aggregation activity, anti-infective activity, anti-atherosclerotic activity, and anti-oxidant activity.

In various embodiments, the herbal compositions further comprise a biologically active ingredient selected from the group consisting of:

a compound selected from the group consisting of Glucosamine, Glucosamine salts, Chondroitin, Methylsulfonylmethane (MSM), Hyaluronic acid, collagen, polyglycans, Chitosan, Undenatured collagen type-II, SAM-e, NEM, quercetin, boron, manganese, ascorbic acid, ascorbic acid salts, flavonoids, alkaloids, phytosterols, terpenes, omega 3 fatty acids and mixtures thereof;

an extract selected from the group consisting of an extract of *Withania somnifera*, an extract of *Sphaeranthus indicus*, an extract of *Boswellia serrata*, an extract of *Curcuma longa*, an extract of *Psidium guajava*, an extract of pine bark, an extract of *Piper nigrum*, an extract of *Piper longum*, and mixtures thereof; and mixtures thereof In various embodiments, an herbal composition comprises an extract of *Annona squamosa*, comprising from 0.01% to 50% by weight of at least one acetogenin compound, and at least one active ingredient selected from the group consisting of an extract of *Boswellia serrata*, an extract of *Psidium guajava*, an extract of *curcuma longa*; ascorbic acid or a salt thereof; an omega-3 fatty acid or a salt or ester thereof; glucosamine or a salt thereof, bromelain, and mixtures thereof.

According to various embodiments disclosed herein, the extract of *Annona squamosa* is obtained by extraction of at least one plant part of *Annona squamosa* with water or an organic solvent;

said at least one plant part being selected from the group consisting of leaves, fruits, seeds, flowers, stem, bark, root, hardwood or mixtures thereof, preferably leaves.

According to various embodiments disclosed herein, the extract of *Annona squamosa* is obtained by extraction of at least one plant part of *Annona squamosa* with a solvent selected from the group consisting of hexane, petroleum ether, ethyl ether, dichloromethane, chloroform, ethyl acetate, acetone, acetonitrile, methanol, ethanol, propanol, n-butanol, iso-propanol, methyl isobutyl ketone, water and mixtures thereof;

said at least one plant part being selected from the group consisting of leaves, fruits, seeds, flowers, stem, bark, root, hardwood or mixtures thereof, preferably leaves.

According to various embodiments disclosed herein, the extract of *Annona squamosa* is obtained by extraction of at least one plant part of *Annona squamosa* with water or an organic solvent to obtain an intermediate product;

said at least one plant part being selected from the group consisting of leaves, fruits, seeds, flowers, stem, bark, root, hardwood or mixtures thereof; and subsequently fractionating said intermediate product using at least one separation technique selected from the group consisting of solvent partitioning, precipitation, crystallization, normal phase chromatography, reversed phase chromatography, size exclusion chromatography, ion exchange chromatography and combinations thereof.

According to various embodiments disclosed herein, acetogenins may be isolated from extracts of at least one plant part of *Annona squamosa*. The isolated acetogenins are found to have biological activity. Various embodiments disclosed herein relate to pharmaceutical or neutraceutical compositions comprising isolated acetogenins, such as acetogenins selected from the group consisting of compound 1, compound 2, compound 3, compound 4, compound 5, compound 6, compound 7, compound 8, compound 9, compound 10, compound 11, and mixtures thereof, where the structures of compounds 1 through 11 are presented in FIGS. 2A and 2B. In various embodiments, the pharmaceutical or neutraceutical compositions may contain the acetogenins alone or in combination with at least one biologically active ingredient selected from the group consisting of Glucosamine, Glucosamine salts, Chondroitin, Methylsulfonylmethane (MSM), Hyaluronic acid, collagen, polyglycans, Chitosan, Undenatured collagen type-II, SAM-e, NEM, quercetin, boron, manganese, ascorbic acid, ascorbic acid salts, flavonoids, alkaloids, phytosterols, terpenes, omega 3 fatty acids, an extract of *Withania somnifera*, an extract of *Sphaeranthus indicus*, an extract of *Boswellia serrata*, an extract of *Curcuma longa*, an extract of *Psidium guajava*, an extract of pine bark, an extract of *Piper nigrum*, an extract of *Piper longum*, and mixtures thereof.

According to some embodiments, the current disclosure provides composition(s) comprising at least one component selected from the extract(s) or fraction(s) standardized to acetogenin(s) having terminal $\alpha,\beta$-unsaturated-$\gamma$-methyl-$\gamma$-lactone moiety derived from *Annona squamosa* in combination with at least one component selected from biologically active ingredient derived from plants/animals/microorganisms; pharmaceutically or dietetically acceptable active ingredients, vitamins, amino acids, minerals; pharmaceutically or dietetically acceptable excipients, vehicles, carriers and diluents or mixtures thereof for prevention, treatment, inhibition or controlling inflammation and/or immune related diseases mediated through cytokines/chemokines or other diagnostic/biomarkers.

In other aspects, the current disclosure provides acetogenin compound(s), extract(s) or fraction(s) derived from *Annona squamosa* leaf comprising acetogenin compound(s) or their composition(s) for the prevention, inhibition or controlling inflammation and/or immune related diseases in a subject in need.

In various embodiments, the current disclosure provides acetogenin compound(s), extract(s) or fraction(s) derived from *Annona squamosa* leaf comprising acetogenin compound(s) or their composition(s) for the prevention, inhibition or controlling metabolic disorders in a subject in need.

In other embodiments, the acetogenin compound(s), extract(s) or fraction(s) derived from *Annona squamosa* leaf comprising acetogenin compound(s) or their composition(s) described herein are useful for regulating/modulating the expression or production of one or more cytokines/chemokines/biomarkers selected from TNF-$\alpha$, IL-1$\beta$, IL-2, IL-4, IL-6, IL-13, MCP-1, Rantes, Eotaxin, ICAM, VCAM, aP2, FLAP, CRP, CD36, 5-Lipoxygenase and MMPs.

DETAILED DESCRIPTION

Figure 1:
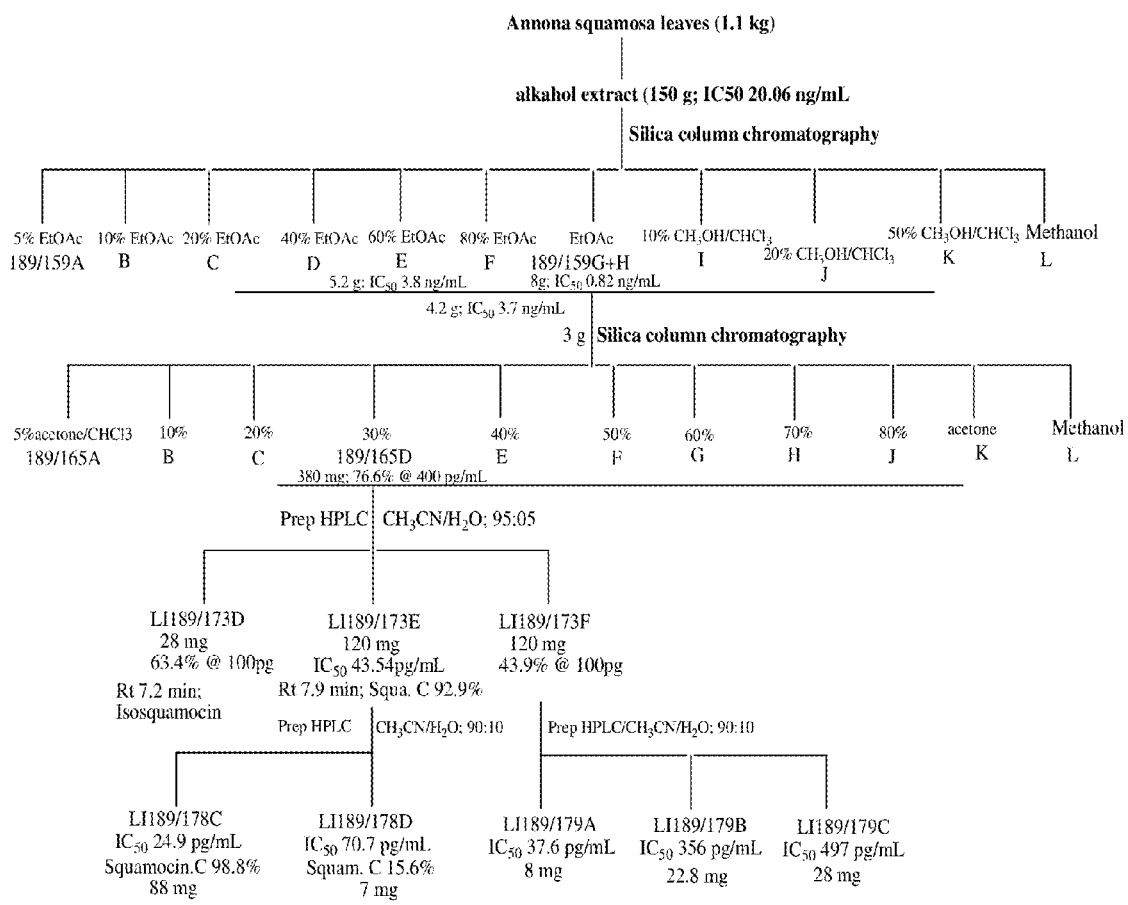
FIG. 1: Figure shows summary depiction of the bioassay guided fraction to identify most active compound and active fractions.

Inflammation is a response of vascular tissues to stimuli such as pathogens, damaged cells or allergic agents, which enter into the body. It is a protective mechanism in the body to remove harmful pathogens or agents and protect the tissues. Pro-inflammatory cytokines such as TNFα, IL-1β, IL-6, GM-CSF and CD4+, Th2 subset derived IL-4, IL-5 and IL-13 lymphokines are considered as the key factors of immunopathogenesis of inflammatory diseases. 5-Lipoxygenase is an enzyme critical for leukotriene synthesis from arachidonic acid, a key step in the inflammatory process. Leukotrienes are key mediators of inflammatory disease.

The activation and gene expression of 5-lipoxygenase (5-LOX) is responsible for the disease condition. The 5-Lipoxygenase activating protein (FLAP) is an 18 kDa integral membrane protein which activates 5-Lipoxygenase by specifically binding arachidonic acid and transferring it to the enzyme. FLAP is therefore responsible for the production of leukotrienes. Hence blocking or down regulating 5-LOX and FLAP is an effective therapeutic approach for the treatment and/or control of inflammatory condition.

Tumor necrosis factor-alpha (TNFα) is an important pleiotropic proinflammatory cytokine. It serves a variety of functions and its expression and production appears to have an effect on most organs of the body. It is produced predominantly by macrophages. TNFα is an acute phase protein and chemotaxin, which initiates a cascade of cytokines and increases vascular permeability, thereby recruiting macrophage and neutrophils to the site of infection. TNFα possesses both growth stimulating properties and growth inhibitory processes, and it appears to have self-regulatory properties as well. The beneficial functions of TNFα include its role in the immune response to bacterial, and certain fungal, viral, and parasitic invasions as well as its role in the necrosis of specific tumors. High levels of TNFα, however, will have detrimental effects and lead to many disease conditions. High levels of TNFα correlate with increased risk of mortality.

Hence, TNFα is an important target for developing novel treatments against a wide range of inflammatory diseases.

Atherosclerosis is also an inflammatory disease characterized by the formation of arterial lesions over a period of several decades at sites of endothelial cell dysfunction. Inflammation plays important role at many stages of atherosclerotic plaque development. Hence, identifying compounds having novel anti-inflammatory properties is a best strategy to target atherosclerosis.

Matrix Metalloproteinases (MMPs) are zinc dependent endopeptidases, that are capable of breaking down all kinds of extra cellular matrix proteins, such as collagen, that are normally found in the spaces between cells in tissues. MMPs are divided primarily into three principal groups, the fibroblast collagenase-1 (MMP-1) formed of the collagenases, the gelatinases comprising gelatinase A (MMP-2) and the gelatinase B (MMP-9), and the stromelysines comprising stromelysine-1 (MMP-3) and matrilysine (MMP-7). An excess of metalloproteinase leads to degradation of biomolecules such as collagen, proteoglycon and gelatin, which can have fatal consequences on epidermis and can also generate diseases of the cartilages, inflammation etc.

There is ever increasing prevalence of various inflammatory diseases and the metabolic disorders. This in conjunction with the urgent need for the control of inflammatory diseases and the metabolic disorders, the research activities in these areas have become high priority targets for numerous scientists around the world. This has created a special interest in finding alternative solutions, especially those based on products of plant origin. The plant derived products are considered to be natural and safe, in contrast with the commercial drugs of synthetic origin. The inventors have thus conducted a detailed investigation involving several in vitro and in vivo experiments on several plant extracts, fractions and pure compounds and accidentally found that administration of the extract(s) or the active fraction(s) or active compounds of the *Annona squamosa* or their compositions in a therapeutically effective amount in cell based studies potently ameliorated the levels of certain cytokines/chemokines/biomarkers that are over expressed during inflammation and/or metabolic/immune disorders.

Various codes of *Annona squamosa* extracts/fractions used to describe the embodiments in the specification and claims are given below:

LI12100—Methanol extract of *Annona squamosa* leaf

LI12100A—Hexane extract obtained by sequential extraction of *Annona squamosa* leaf LI12100B—Methanol extract obtained by sequential extraction of *Annona squamosa* leaf LI12100C—Ethyl acetate extract of *Annona squamosa* leaf LI12100D—Ethanol extract of *Annona squamosa* leaf LI12100E—Hydroalcohol extract of *Annona squamosa* leaf LI12100F—Ethyl acetate extract of *Annona squamosa* leaf obtained by partitioning LI12100G—Hexane extract of *Annona squamosa* seed LI12100H—Ethyl acetate extract of *Annona squamosa* seed LI12100I—Mixture of Methanol extract and Water extract of *Annona squamosa* leaf LI12100J—Mixture of methanol extracts of leaves and seeds of *Annona squamosa*

LI12101—Ethyl acetate extract obtained by partitioning of *Annona squamosa* leaf LI189/159G+H—Is an active fraction obtained by chromotagraphy of the methanol extract of *Annona squamosa* leaf (LI12100).

A wide range of plant extracts were screened for their inhibitory potential against the pro-inflammatory cytokine TNFα in THP-1 human monocytes cells. The extracts of *Annona squamosa* unexpectedly showed most potent TNFα inhibition among the extracts tested. The methanol extract (LI12100) derived from the leaves of *Annona squamosa* potently inhibited TNFα with a half inhibitory concentration ($IC_{50}$) of 20.06 ng/mL. The ethyl acetate extract (LI12101) obtained through a selected process from the leaves of *Annona squamosa* has also shown most potent TNFα inhibition with an $IC_{50}$ value of 8.34 ng/mL. The other extracts (LI12100A to LI12100J) of *Annona squamosa* also showed potent TNFα inhibition as summarized in Table 1.

The methanol extract (LI12100) of *Annona squamosa* was subjected bioassay guided separation to identify the compound responsible for the TNFα inhibition and to produce the fractions having improved activity. LI12100 was subjected to silica flash column chromatography using ethyl acetate/hexane mixtures as eluants. The fractions eluted with 60% and 80% ethyl acetate/hexane mixtures and ethyl acetate have shown potent activity. The fraction (LI189/159G+H) eluted with ethyl acetate has however shown superior TNFα inhibition ($IC_{50}$ 0.82 ng/mL). This active fraction was subjected to further purification again on silica flash column using acetone/chloroform mixtures, followed by preparative HPLC purification of the active fraction on Phenomenex Luna column (10μ, C18, 250 mm×21.2) first using 95: 5 acetonitrile/water mixture and finally with 90: 10 acetonitrile/water mixture to obtain a pure compound (LI12103) having an $IC_{50}$ value of 24.9 μg/mL. By a critical analysis of its $^1H$ NMR, $^{13}C$ NMR and Mass spectral data and comparison with the values reported in literature, its chemical structure was found unexpectedly to be an acetogenin compound called squamocin C (LI12103; 1). A minor compound having 63% TNFα inhibition at 100 pg/mL was also isolated from the same fraction and its structure was identified as isosquamocin (LI12132; 2). The bioassay guided fractionation is summarized in FIG. 1.

Figure 2A:
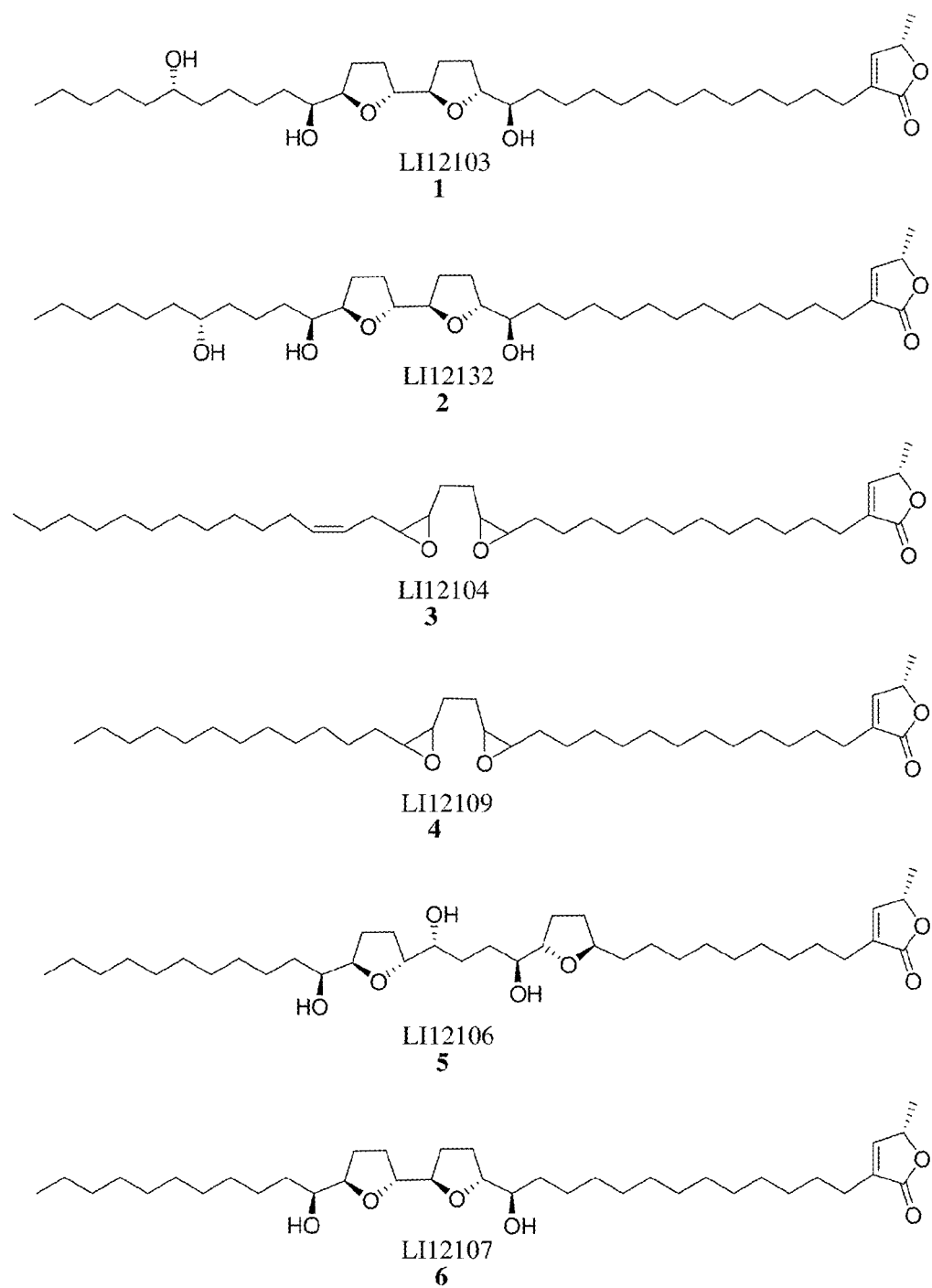
FIGS. 2A and 2B: Figure shows the chemical structures of acetogenins isolated from the extracts of the leaves of *Annona squamosa*.
Figure 2B:
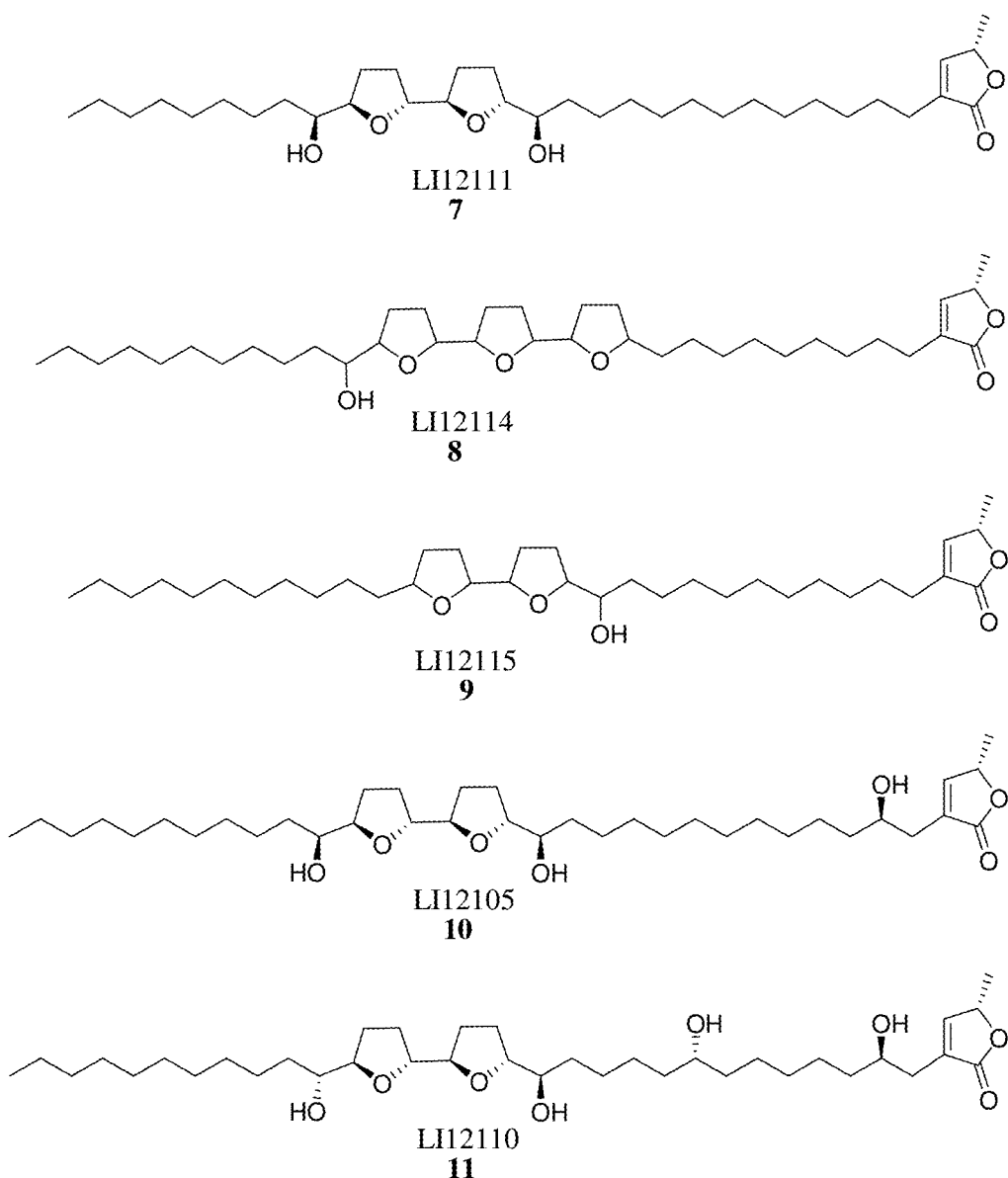

The ethyl acetate extract (LI12101) of the leaves obtained through a selected process was also subjected to more detailed bio-assay guided fractionation and/or purification to isolate and identify other acetogenin compound(s) that are responsible for the anti-TNFα activity using repeated flash column chromatography over silica gel using mixtures of organic solvents and preparative HPLC purification. This tedious and laborious purification process yielded closely 15 acetogenin compounds comprising terminal α,β-unsaturated-γ-methyl-γ-lactone moiety having atleast one functional group selected from one or more tetrahydrofuran moieties, one or more epoxide moieties, one or more hydroxyl groups, and one or more olefinic bonds (double bonds) in the alkyl chain. The compounds include squamocin C (1), isosquamocin (LI12132; 2), dieposabadelin (LI12109; 4), squamostatin D (LI12106; 5), squamocin L (LI12107; 6), squamocin J (LI12111; 7), squamocin G (LI12105; 10), and 10-hydroxyasimicin (LI12110; 11). The structures of compound LI12104 (3), compound LI12114 (8), compound LI12115 (9) are assigned tentatively. The structures of the known compounds and those assigned tentatively are summarized in FIGS. 2A and 2B.

The remaining compounds, compound LI12112, compound LI12113, compound LI12116 and compound LI12117 are also characterized to be annonaceous acetogenins with characteristic terminal α,β-unsaturated-γ-methyl-γ-lactone as per the spectral data provided in the experimental section in Example 13, LI12112 is an acetogenin with characteristic terminal α,β-unsaturated-γ-methyl-γ-lactone and contains a tetrahydrofuran moiety, three hydroxyl groups and a disubstituted double bond on the alkyl chain. It has a molecular weight (MW) of 606 mass units. The spectral data of this compound is summarized below:

LI12112: $^1H$ NMR (CDCl$_3$, 400 MHz): δ 6.98 (1H, d, J=1.2 Hz), 5.36 (2H, m), 4.99 (1H, qd, J=1.6, 6.8 Hz), 3.87 (4H, m), 3.41 (2H, m), 2.36-2.24 (4H, m), 2.06-1.90 (5H, m), 1.68-1.50 (8H, m), 1.41 (3H, d, J=6.8 Hz), 1.25 (s), 0.88 (3H, t, J=6.8 Hz); LCMS: 629 (M+Na)$^+$+ve ion mode.

LI12113 is an acetogenin with molecular weight of 588 mass units and contains characteristic terminal α,β-unsaturated-γ-methyl-γ-lactone and possesses three epoxide groups on the alkyl chain. The spectral data of this compound is summarized below:

LI12113: 1H NMR (CDCl3, 400 MHz): δ 6.98 (1H, d, J=1.6 Hz), 4.99 (1H, qd, J=1.6, 6.8 Hz), 3.03-2.92 (6H, m), 2.26 (2H, t, J=7.6 Hz), 2.04-1.95 (2H, m), 1.84 (2H, m), 1.78 (2H, m), 1.66-1.47 (10H, m), 1.40 (3H, d, J=6.8 Hz), 1.26 (s), 0.88 (3H, t, J=6.8 Hz); 13C NMR (CDCl3, 100 MHz): δ 173.7, 148.7, 138.4, 57.3, 56.8, 56.6, 31.9, 29.7, 29.5, 29.5, 29.3, 29.2, 27.8, 27.4, 26.6, 25.3, 25.2, 25.2, 22.6, 19.2, 14.1; LCMS: 611 (M+Na)$^+$+ve ion mode.

LI12116 (MW 604) is an acetogenin with characteristic terminal α,β-unsaturated-γ-methyl-γ-lactone and contains two epoxide groups and a hydroxyl group on the alkyl chain. The spectral data of this compound is summarized below:

LI12116: 1H NMR (CDCl3, 400 MHz): δ 6.98 (1H, s), 4.99 (1H, qd, J=6.4, 1.6 Hz), 4.29 (1H, m) 2.98 (4H, m), 2.27 (2H, t, J=8.0 Hz), 2.07 (2H, m), 1.77 (6H, m), 1.55 (10H, m), 1.41 (3H, d, J=6.8 Hz), 1.26 (s), 0.88 (3H, t, J=6.8 Hz); LCMS: 627 (M+Na)$^+$+ve ion mode.

LI12117 is an acetogenin with characteristic terminal α,β-unsaturated-γ-methyl-γ-lactone and contains two tetrahydrofuran moieties three hydroxyl groups on alkyl chain. The spectral data of this compound is summarized below:

LI12117: 1H NMR (CDCl3, 400 MHz): δ 6.98 (1H, d, J=1.2 Hz), 5.35 (2H, m) 4.98 (1H, qd, J=6.8, 1.6 Hz), 4.16 (1H, m), 3.93-3.82 (4H, m), 3.56 (1H, m), 3.40 (1H, m), 2.29 (3H, m), 2.06 (4H, m), 1.67-1.50 (16H, m), 1.40 (3H, d, J=6.8 Hz), 1.26 (s), 0.88 (3H, t, J=6.8 Hz); LCMS: 643 (M+Na)$^+$+ve ion mode.

The biologically active acetogenin compounds disclosed herein have characteristic structural features, wherein each of said acetogenin comprise a terminal α,β-unsaturated-γ-methyl-γ-lactone moiety (a). In addition the said acetogenins comprise one or more tetrahydrofuranic (b) group(s) or one or more epoxide (c) group(s) shown below in the alkyl chain, further containing optionally one or more hydroxyl groups and/or one or more olefinic bonds (double bonds).

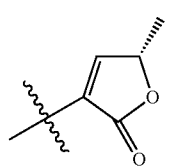

a

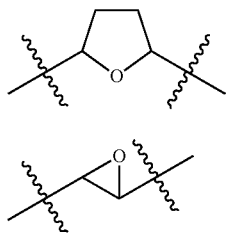

A few of the acetogenin compounds exhibited very potent TNFα inhibition with 50% inhibitory concentrations ($IC_{50}$) at nanomolar and sub-nanomolar concentrations. The data summarized in Table 1 clearly suggests that the acetogenin composition is responsible for the activity of the extracts and fractions derived from *Annona squamosa* leaf.

The extracts of the leaves of *Annona squamosa* were then standardized to squamocin C. The methanol extract (LI12100) as described above contains 0.4% of squamocin C, 0.07% of squamosin G and 0.08% of squamocin L. The ethyl acetate extract (LI12101) as described above contains 0.5% of squamocin C. The concentration of the individual acetogenins and the total concentration vary based on the nature of the raw material used for the extraction. However, an extract having as low as 0.1% of squamocin C showed potent TNFα inhibition in vitro and potent anti-inflammatory activity in vivo The total concentration of the 'acetogenin compounds containing 'terminal α,β-unsaturated-γ-methyl-γ-lactone moiety' as described above was found to be in the range of 0.2% to 5%.

The inhibition of matrix metalloproteinase-3 (MMP-3) production by *Annona squamosa* ethyl acetate extract (LI12101) and other extracts comprising novel acetogenin composition were evaluated in Interleukin-13 induced human lung tumor cell line A549. The extracts potently inhibited the MMP-3 production suggesting that the extracts and fractions comprising novel acetogenin composition can be useful to prevent cartilage degradation and improve joint health.

The potent in vitro anti-inflammatory efficacy shown by the *Annona squamosa* leaf ethyl acetate extract (LI12101; standardized to 0.2% squamocin C) was then tested in an in vivo system using Freund's Complete Adjuvant induced arthritis model of Sprague Dawley rats. The anti-inflammatory efficacy of LI12101 (100 mg/kg body weight per day) was evaluated in Freund's Complete Adjuvant induced arthritis model of Sprague Dawley rats and compared its efficacy with that shown by the positive control group supplemented with Prednisolone at 10 mg/kg body weight. The treatment group rats were supplemented daily with LI12101 or prednisolone. At the 14th day, Freund's Complete Adjuvant (FCA) was injected subcutaneously in the sub-plantar region of the left hind paw of each animal. The experiment was terminated on 28th day. Blood samples were collected from each animal at regular intervals and paw volumes were measured by Plethysmography equipment on the day of FCA injection and after 13 days of FCA inoculation. The difference in volume of paw edema is considered as the inflammatory response. The in vivo anti-inflammatory responses of LI12101 and prednisolone were estimated by calculating the percentage of inhibition of paw edema when compared to the CMC supplemented control.

Figure 3:
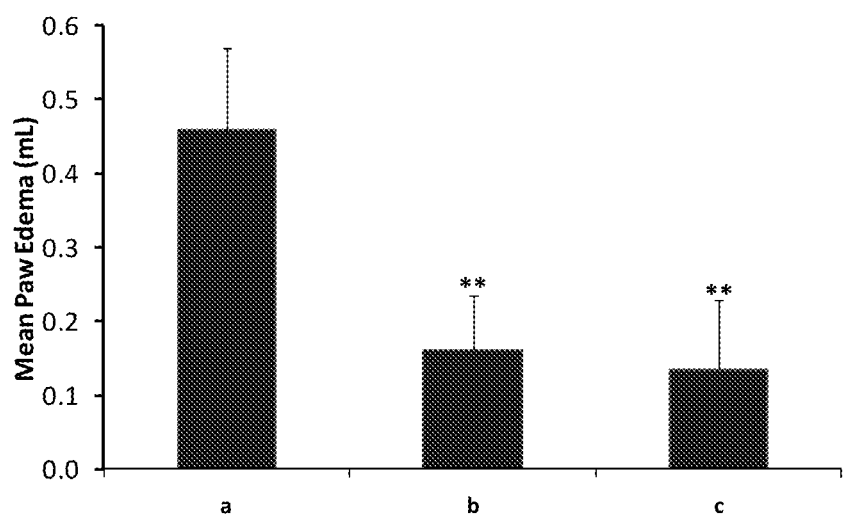
FIG. 3: Figure shows bar diagrammatic representation of paw volumes of Freund's Complete Adjuvant induced paw edema in Sprague Dawley rats by the ethyl acetate extract of *Annona squamosa* leaf (LI12101, 100 mg/kg) and Prednisolone (10 mg/kg). The bars a, b and c correspond to the paw volumes in groups treated with control, LI12101 and Prednisolone respectively. Each bar represents mean±SD, N=6. ** $p<0.005$ (vs. control).
Figure 4:
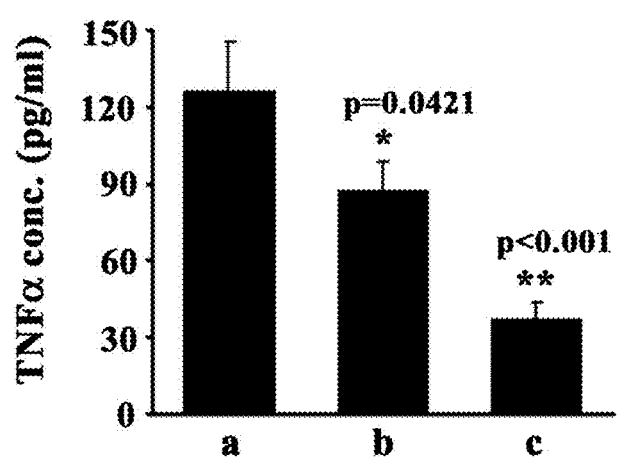
FIG. 4: Figure shows bar diagrammatic representation of serum TNF$\alpha$ concentrations in different groups of animals. After 14 days of FCA challenge, serum TNF$\alpha$ was quantitatively measured by enzyme-immuno assay kit (R&D Systems, USA). The bars a, b and c represent the levels of the cytokines in groups supplemented with control, LI12101 (100 mg/kg) and prednisolone (10 mg/kg) respectively. Each bar represents mean±SD, N=6. * $p<0.05$ and ** $p<0.005$ (vs. control).

The treatment group supplemented with LI12101 showed 65% reduction in paw volume, when compared to the control group. The positive control group supplemented with prednisolone exhibited 71% inhibition at 10 mg/kg dose level as summarized in FIG. 3. Further, the levels of biomarker, tumor necrosis factor-alpha (TNFα) in the serum of the treatment groups and the control group were also evaluated. The treatment group supplemented with LI12101 showed significant reduction in the serum biomarker TNFα compared to the level exhibited by control group supplemented with 0.5% CMC as shown in FIG. 4.

To further confirm the in vivo anti-inflammatory activity and study the dose dependent effect, the methanol extract of *Annona squamosa* leaves (LI12100; standardized to 0.24% squamocin C) was evaluated in Freund's Complete Adjuvant induced arthritis model of Sprague Dawley rats. The anti-inflammatory efficacy of LI12100 (at 50 mg/kg and 100 mg/kg body weight per day) was evaluated in FCA induced arthritis model of Sprague Dawley rats and compared its efficacy with that shown by the positive control group supplemented with Prednisolone at 10 mg/kg body weight. The study was conducted and the paw edema inhibition evaluated as described above.

Figure 5:
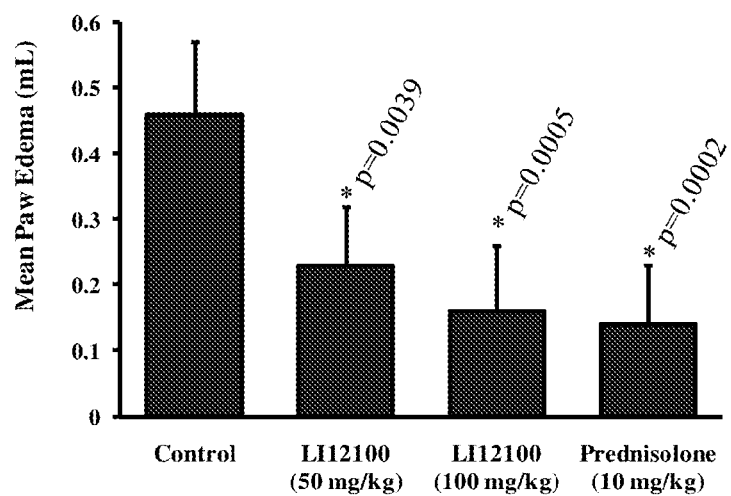
FIG. 5: Figure shows bar diagrammatic representation of paw volumes of Freund's Complete Adjuvant induced paw edema in Sprague Dawley rats by methanol extract of *Annona squamosa* leaf (LI12100) at 50 mg/kg or 100 mg/kg body weight and Prednisolone (10 mg/kg). The bars correspond to the paw volumes in groups treated with control, LI12100 at 50 mg/kg body weight, LI12100 at 100 mg/kg body weight and prednisolone respectively. Each bar represents mean±SD, N=6.
Figure 6:
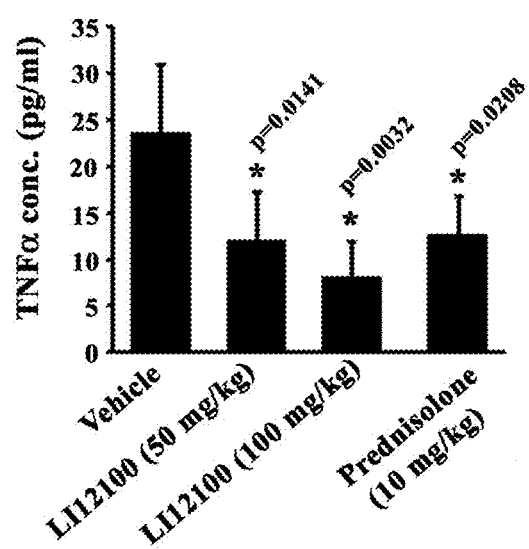
FIG. 6: Figure shows bar diagrammatic representation of serum TNFα concentrations in different groups of animals. After 14 days of FCA challenge, serum TNFα was quantitatively measured by enzyme-immuno assay kit (R&D Systems, USA). The bars represent the levels of the cytokines in groups supplemented with control, LI12100 at 50 mg/kg body weight, LI12100 at 100 mg/kg body weight and prednisolone (10 mg/kg) respectively. Each bar represents mean±SD, N=6.

The treatment group supplemented with LI12100 showed dose dependent efficacy and exhibited 49.5% and 64.5% reduction in paw volume at 50 mg/kg and 100 mg/kg body weight respectively, when compared to the control group. The positive control prednisolone (10 mg/kg body weight) exhibited 69.2% (10 mg/kg body weight) reduction in paw volume as summarized in FIG. 5. The levels of biomarker, tumor necrosis factor-alpha (TNF-α) in the serum of the treatment groups and the control group were also evaluated. The treatment group supplemented with LI12100 at both the doses showed significant reduction in the serum biomarker TNFα compared to the level exhibited by control group supplemented with 0.5% CMC as shown in FIG. 6.

Further, the levels of a wide range of cytokine biomarkers were estimated in the serum of the treatment groups supplemented with LI12100 and the control group using multiplex assay (RCYTOMAG 80K) following the instructions provided by the vendor (Millipore Corporation, Billerica, Mass., USA). The treatment groups supplemented with LI12100 significantly modulated the expression of many cytokines in the serum, when compared to their respective levels exhibited by control group. The cytokines modulated by LI12100 include TNFα, IFNγ, IL-1β, IL-2, IL-4, IL-6, IL-13, MCP-1, Rantes and Eotaxin. This unexpected result suggest that the extracts of *Annona squamosa* are useful for prevention, treatment, inhibition or controlling inflammation and/or immune related diseases mediated through these cytokines/chemokines and/or biomarkers.

The foregoing discussion clearly establishes that acetogenin compound(s) having the terminal α,β-unsaturated-γ-methyl-γ-lactone moiety, the *Annona squamosa* derived extract(s) or fraction(s) containing acetogenin compound(s) comprising the terminal α,β-unsaturated-γ-methyl-γ-lactone moiety and their compositions are potent regulators or modulators of cytokines/chemokines or biomarker proteins such as TNFα, IL-1β, IL-2, IL-4, IL-6, IL-13, MCP-1, Rantes, Eotaxin, ICAM, VCAM, aP2, FLAP, CRP, CD36, 5-Lipoxygenase and MMPs and the same can be used for prevention, treatment, inhibition or controlling inflammation and disease conditions related to inflammation or immune disorders.

The ethyl acetate extract (LI12101) and methanol extract (LI12100) derived from *Annona squamosa* leaves containing acetogenins composition was used in the current disclosure to demonstrate the in vitro and in vivo efficacy. However, acetogenin compound(s) or other *Annona squamosa* derived extracts and/or fractions standardized to acetogenin(s) comprising terminal α,β-unsaturated-γ-methyl-γ-lactone moiety in combination with atleast one functional group selected from tetrahydrofuran moiety or epoxide moiety or hydroxyl group or olefinic group in the alkyl chain also showed potent anti-TNFα activity (Table 1).

The hexane (LI12100G) and ethyl acetate (LI12100H) extracts of the seeds of Annona squamosa also showed potent TNFα inhibition with $IC_{50}$ values of 3.1 ng/mL and 2.3 ng/mL respectively (Table 1).

Several new compositions (Composition-1A/1B to composition-10A/10B) comprising at least one component selected from the extract(s) or fraction(s) standardized to acetogenin(s) derived from Annona squamosa comprising atleast terminal α,β-unsaturated-γ-methyl-γ-lactone moiety having at least one component selected from biologically active ingredient derived from plants/animals/microorganisms; pharmaceutically or dietetically acceptable active ingredients, vitamins were prepared for biological evaluation and for use in prevention, treatment, inhibition or controlling inflammation and/or immune related diseases mediated through cytokines/chemokines or other biomarkers.

The solvent(s) for the extraction of plants parts of Annona squamosa include but not limited to hexane, ethyl acetate, ethyl ether, chloroform, acetone, methyl isobutyl ketone (MIBK), methanol, ethanol, isopropanol, n-butanol, liquid carbon dioxide, water or mixtures thereof.

The extracts derived from fruits, seeds, flowers, stem, bark, root, hardwood and other aerial plant parts derived from Annona squamosa can also be used.

One of the key developments in obesity research has been the general recognition that obesity is a chronic low-level inflammation. The link between obesity and inflammation has been obvious from the increased plasma levels of several inflammatory markers including cytokines (TNFα, IL-6) and acute phase proteins like C-reactive protein (CRP) in obese individuals. It has also been theorized in recent years that chronic, low-grade tissue inflammation related to obesity contributes to insulin resistance, the major cause of Type 2 diabetes.

The Annona squamosa extracts comprising acetogenins were screened for their inhibitory potential against the lipid accumulation in 3T3-L1 mouse adipocyte cells. The extracts of Annona squamosa unexpectedly showed potent anti-adipogenesis and prolipolytic activity in cell based in vitro assays on 3T3-L1 cells. The ethyl acetate extract (LI12101) has shown 46.6% inhibition of lipid accumulation at 10 μg/mL concentration. The other extracts also showed potent anti-adipogenesis activity as summarized in Table 4.

The inventors have then evaluated the modulation of metabolic biomarkers that are primarily responsible for the adipogenesis processes, insulin resistance in type 2 diabetes, obesity, metabolic syndrome or other metabolic disorders by the methanolic extract (LI12100) of Annona squamosa using an immunoblot assay.

Figure 7:
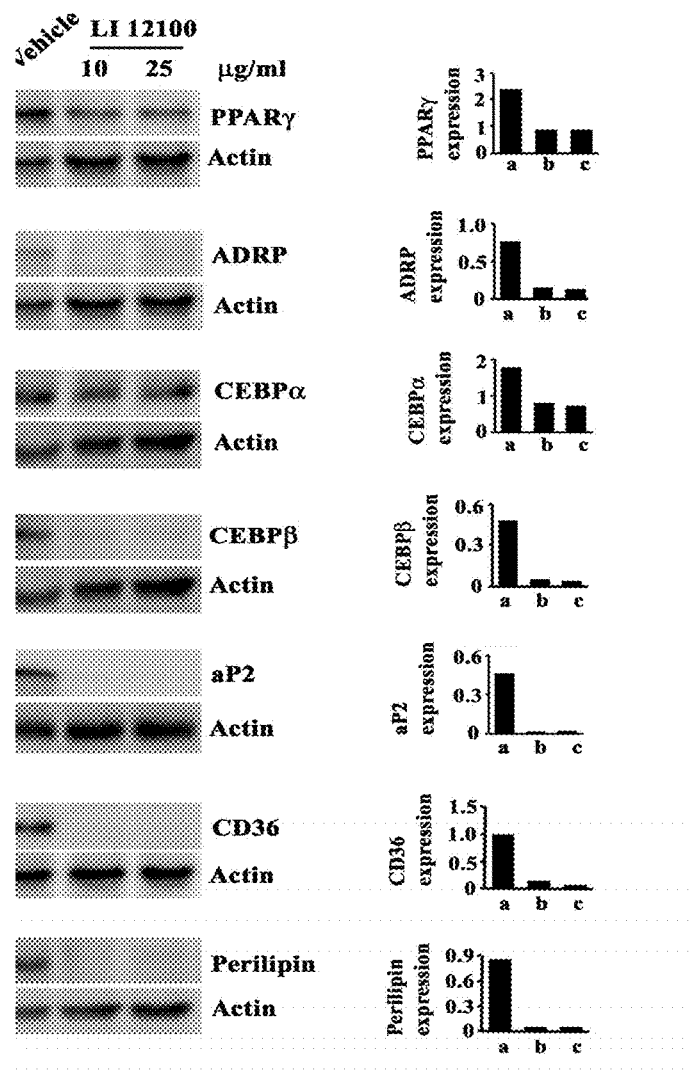
FIG. 7: Modulation of metabolic markers Adipogenesis and Lipolysis processes in 3T3-L1 adipocytes by *Annona squamosa* leaf methanol extract (LI12100). Representative immunoblots depict down-regulation of various marker proteins such as PPARγ, ADRP, CEBPα, CEBPβ, aP2, CD36 and perilipin as indicated. The 3T3-L1 mouse pre-adipocytes were allowed to differentiate in absence or presence of 10 µg/ml or 25 µg/ml of LI12100. Vehicle control cultures received only similar concentrations of DMSO. Expression of actin protein was evaluated in each blot as the internal control. Expression of each protein was measured densitometrically and normalized with actin expression. The comparative expression levels in arbitrary units are represented as bar diagrams (side panels). The bars a, b and c represent the expressions in cells treated with vehicle control, 10 µg/ml of LI12100 and 25 µg/ml of LI12100 respectively.

It was found that the methanol extract of Annona squamosa (LI12100) potently modulated the levels of several adipocyte differentiation markers such as Peroxisome proliferator-activated receptor gamma (PPARγ), ADRP, CEBPα, CEBPβ, CD36, Fatty Acid Binding Protein 4 (aP2/FABP4), and intracellular lipid droplet surface associated protein (perilipin) (FIG. 7) in a dose dependent manner. The down regulation of these marker proteins in LI12100 treated adipocytes suggests that the methanol extract of Annona squamosa exerts multiple beneficial roles in controlling the adipogenic differentiation process; by (1) inhibiting cellular differentiation by down regulating PPARγ, which is a nuclear receptor protein that functions as a transcription factor for regulation of cellular differentiation, development and metabolism, (2) restricting cholesterol ester uptake by inhibiting CD36, which is a class B scavenger receptor involved in lipid uptake, (3) decreasing intracellular adiposity and intracellular lipid transport by reducing FABP4/aP2 level, which acts as a transport protein for long chain fatty acids and by (4) inhibiting adipose differentiation related protein (ADRP), which play possible role in the formation or stabilization of lipid droplets in adipocytes and enhances uptake of long chain fatty acids by adipose tissue.

Moreover, down regulation of perilipin protein in LI12100 treated adipocytes strongly indicate reduced fat store in the cytoplasm. Perilipin is a protein that coats lipid droplets in adipocytes. It offers protection from the action of hormone-sensitive lipase, which breaks triglycerides into glycerol and free fatty acids for use in metabolism or lipolysis. Therefore it is indicative that methanol extract of Annona squamosa provides such a state where the stored lipids are more susceptible to enzymatic break down into glycerol and free fatty acids by thinning the perilipin coat around the lipid filled vesicles. In addition, LI12100 also potently down regulated the adipogenesis differentiation markers CEBPα and CEBPβ. CEBPα and CEBPβ are CCAAT/enhancer-binding protein alpha and beta, respectively. They are proteins involved in different cellular responses like in the control of cellular proliferation, growth, differentiation and metabolism. CEBPβ is transiently induced during the early stages of adipocyte differentiation, whereas CEBPα is upregulated during the terminal stages adipogenesis. CEBPα is required for both adipogenesis and normal adipocyte function. Hence, CEBPα and CEBPβ are PPARγ-inducible gene products, related to adipocytes differentiation process and they are important targets for controlling metabolic disorders. Their down regulation by LI12100 suggests that Annona squamosa extracts could be potential agents for the prevention, treatment, inhibition or controlling metabolic diseases/disorders Similarly, the modulation of adiponectin protein by LI12100 in 3T3-L1 adipocytes was evaluated in Western immunoblot assay. The cell culture, treatment protocol and immunoblot assay methodology were as per the standard protocol. The extract LI12100 also showed potent upregulation of adiponectin protein expression in 3T3-L1 mature adipocytes. LI12100 at 5 μg/mL and 10 μg/mL showed 38% and 64% improvements in serum adiponectin concentration respectively. Adiponectin is a hormone secreted by adipocytes. It reduces intracellular triglyceride content and up-regulates glucose uptake by potentiating insulin signaling, thus it provides protection from both adipogenicity and from developing insulin resistant diabetes or type 2 diabetes. Therefore, our finding indicates that the extracts of Annona squamosa provides protection against developing obesity, insulin resistant or Type 2 diabetes and also helps in attenuating endothelial dysfunction disorders as well. These extracts can thus be useful in the prevention, treatment and control of above metabolic disorders.

The foregoing suggests that the extracts of Annona squamosa could be useful for the prevention, treatment, inhibition or controlling metabolic diseases/disorders through the modulation of one or more metabolic biomarkers. These biomarkers include Peroxisome proliferator-activated receptor gamma (PPARγ), Adipose Differentiation Related Protein (ADRP), CCAAT/enhancer-binding protein alpha (CEBPα), CCAAT/enhancer-binding protein beta (CEBPβ), adipocyte CD36, Macrophage CD36, Monocyte Chemotactic protein (MCP-1), Oxidized LDL (Ox-LDL), adipocyte fatty-acid-binding protein (aP2/FABP4/A-FABP), beta-3 Adrenergic Receptor (β3AR), Perilipin, Adiponectin, Protein tyrosine phosphatase-1B (PTP-1B), Matrix Metalloproteinase-1 (MMP-1), Matrix Metalloproteinase-3 (MMP-3) and Matrix Metalloproteinase-13 (MMP-13).

It is obvious from this unexpected result that acetogenin(s), the extracts and fractions comprising the acetogenin(s) can also be used for the prevention, control and treatment of metabolic syndrome, obesity, diabetes, atherosclerosis and endothelial dysfunction and other metabolic disorders.

For the purpose of this disclosure the phrase 'extracts/fractions standardized to acetogenin(s) comprising terminal α,β-unsaturated-γ-methyl-γ-lactone moiety' widely used in the specification and the claims of the current disclosure refers to 'extract(s)/fraction(s) derived from *Annona squamosa* that is standardized to contain atleast one acetogenin compound having terminal α,β-unsaturated-γ-methyl-γ-lactone moiety, wherein the α,β-unsaturated-γ-methyl-γ-lactone moiety is located at the end of the alkyl chain and the said acetogenin further contains one or more functional groups selected from tetrahydrofuran moiety/moieties, epoxide/epoxides, hydroxyl group(s), olefinic group(s).

For the purpose of this disclosure, the word "component" widely used in the specification and claims of the current disclosure, unless otherwise stated, refers to at least one acetogenin compound having terminal α,β-unsaturated-γ-methyl-γ-lactone moiety derived from *Annona squamosa* or the extracts or fraction standardized to acetogenin(s) having terminal α,β-unsaturated-γ-methyl-γ-lactone moiety derived from *Annona squamosa* or mixtures thereof.

The word 'moiety' or 'group' used in the specification and claims of the current disclosure are interchangeable and refer to the functional group or functional moiety.

The word "composition" used in the specification and claims of the current disclosure refers to combination of one or more of acetogenins having terminal α,β-unsaturated-γ-methyl-γ-lactone moiety derived from *Annona squamosa* or the extracts or fraction standardized to acetogenins having terminal α,β-unsaturated-γ-methyl-γ-lactone moiety or both; or mixtures thereof with one or more of other biologically active components, vehicles, carriers and diluents etc.

The phrase "biologically active components" or "biologically active ingredient(s)" refers to extract(s) or fraction(s) or compound(s) derived from plants, animals and/or microorganisms.

Different embodiments of the current disclosure are as outlined below:

In a preferred embodiment, the disclosure provides extract(s) or fraction(s) standardized to acetogenin(s) comprising terminal α,β-unsaturated-γ-methyl-γ-lactone moiety derived from *Annona squamosa* for prevention, treatment, inhibition or controlling one or more inflammations and/or immune related diseases mediated through cytokines/chemokines or other biomarkers.

In another preferred embodiment, the disclosure provides herbal composition(s) having at least one component selected from the extract(s) or fraction(s) standardized to acetogenin(s) comprising terminal α,β-unsaturated-γ-methyl-γ-lactone moiety derived from *Annona squamosa* in combination with at least one component selected from biologically active ingredient derived from plants/animals/microorganisms; pharmaceutically or dietetically acceptable active ingredients, vitamins, amino acids, minerals; pharmaceutically or dietetically acceptable excipients, vehicles, carriers and diluents or mixtures thereof for prevention, treatment, inhibition or controlling one or more inflammations and/or immune related diseases mediated through cytokines/chemokines or other biomarkers.

In another preferred embodiment, the disclosure further provides extract(s) or fraction(s) standardized to acetogenin(s) comprising terminal α,β-unsaturated-γ-methyl-γ-lactone moiety or their composition(s) disclosed herein for the prevention, treatment and/or control inflammation and/or immune related diseases, wherein the inflammation and/or immune related diseases include but not limited to arthritis, asthma, atherosclerosis, endothelial dysfunction, allergic rhinitis, dermatitis, psoriasis, cystic fibrosis, inflammatory bowel diseases, interstitial cystitis, migraine, pain, angina, chronic prostatitis, sun burn, periodontal disease, multiple sclerosis, systemic lupus erythematosis, uveitis, post-angioplasty restenosis, glomerulonephritis, gastrointestinal allergies, nephritis, conjunctivitis, chronic obstructive pulmonary disease, occupational asthma, eczema, bronchitis, hay fever, hives, allergic disorders and for conditions like wheezing, dyspnea, non productive cough, chest tightness, neck muscle tightness, chest pain, joint pain and several other conditions associated thereof in mammals.

In another preferred embodiment, the non-limiting examples of arthritis as mentioned above comprise rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, joint disorders, spondyloarthropathies (ankylosing spondylitis), osteoarthritis, hyperuricemia and arthritis associated with acute gout, chronic gout and systemic lupus erythematosus and degenerative arthritis.

In yet another preferred embodiment, the disclosure provides extract(s) or fraction(s) standardized to acetogenin(s) comprising terminal α,β-unsaturated-γ-methyl-γ-lactone moiety or their compositions for the modulation of the expression or production of one or more cytokines/chemokines or biomarkers/certain redox-sensitive pro-inflammatory genes related to inflammation, immunity and other associated/related diseases, wherein the biomolecules/biomarkers comprise TNFα, IL-1β, IL-2, IL-4, IL-6, IL-13, MCP-1, Rantes, Eotaxin, ICAM, VCAM, aP2, FLAP, CRP, CD36, 5-Lipoxygenase and MMPs.

In another preferred embodiment, the disclosure provides extract(s) or fraction(s) standardized to acetogenin(s) comprising terminal α,β-unsaturated-γ-methyl-γ-lactone moiety disclosed herein for prevention, treatment, inhibition or controlling metabolic diseases/disorders.

In other preferred embodiment, the disclosure provides herbal composition comprising at least one component selected from the extract(s) or fraction(s) standardized to acetogenin(s) comprising terminal α,β-unsaturated-γ-methyl-γ-lactone moiety derived from *Annona squamosa* in combination with at least one component selected from biologically active ingredient derived from plants/animals/microorganisms; pharmaceutically or dietetically acceptable active ingredients, vitamins, amino acids, minerals; pharmaceutically or dietetically acceptable excipients, vehicles, carriers and diluents or mixtures thereof, for prevention, treatment, inhibition or controlling one or more metabolic diseases/disorders.

In another embodiment, the disclosure provides extract(s) or fraction(s) standardized to acetogenin(s) comprising terminal α,β-unsaturated-γ-methyl-γ-lactone moiety, derived from *Annona squamosa* and their compositions, wherein the said acetogenin(s) further comprises atleast one functional group selected from tetrahydrofuranic group(s), epoxide group(s), hydroxyl group(s) and olefinic (double bond) group(s).

In the other embodiment, the metabolic disorders that can be prevented, treated, inhibited or controlled by the extracts or fractions derived from *Annona squamosa* or their compositions disclosed herein can be selected from obesity, over weight, diabetes, atherosclerosis, arteriosclerosis, cardiovascular diseases, hypertension, hypercholesterolemia, hyperlipidemia, hypertriglyceridemia, metabolic syndrome, endothelial dysfunction, insulin resistance, increased insulin sensitivity, hyperinsulinemia, dyslipidemia, low HDL-cholesterol, lipoprotein aberrations, decreased triglycerides, elevated uric acid levels, fatty liver, non-alcoholic fatty liver disease, polycystic ovarian syndrome, haemochromatosis (iron overload), *acanthosis nigricans* (dark patches on the skin), impaired glucose tolerance (IGT), impaired fasting glucose (IFG), cardiovascular diseases and other metabolic disorders.

In other embodiment, the disclosure provides acetogenin(s), the extracts and fractions derived from *Annona squamosa* comprising acetogenin compounds and their compositions for the regulation/modulation of the expression or production of one or more of the cytokines, chemokines or biomarkers of metabolic disorders and other associated and related diseases, comprising Peroxisome proliferator-activated receptor gamma (PPARγ), Adipose Differentiation Related Protein (ADRP), CCAAT/enhancer-binding protein alpha (CEBPα), CCAAT/enhancer-binding protein beta (CEBPβ), adipocyte CD36, Macrophage CD36, Monocyte Chemotactic protein (MCP-1), Oxidized LDL (Ox-LDL), adipocyte fatty-acid-binding protein (aP2/FABP4/A-FABP), beta-3 Adrenergic Receptor (β3AR), Perilipin, Adiponectin, Protein tyrosine phosphatase-1B (PTP-1B), Matrix Metalloproteinase-1 (MMP-1), Matrix Metalloproteinase-3 (MMP-3) and Matrix Metalloproteinase-13 (MMP-13).

In yet another embodiment, the disclosure also provides the method of treating inflammation, immune related diseases/disorders as disclosed herein in subjects or mammals by administering extracts and fractions derived from *Annona squamosa* standardized to acetogenin(s) comprising terminal α,β-unsaturated-γ-methyl-γ-lactone moiety or their composition(s).

In still another embodiment, the disclosure also provides the method of treating metabolic disorders as disclosed herein in subjects or mammals by administering acetogenin compound(s), extract(s) or fraction(s) derived from *Annona squamosa* standardized to acetogenin(s) comprising terminal α,β-unsaturated-γ-methyl-γ-lactone moiety or their composition(s).

In another embodiment, the disclosure relates to the use of acetogenin compound(s) or their composition(s) in preparation of various pharmaceuticals, dietary supplements, food ingredients and beverages.

In another embodiment, the disclosure provides extract(s) and fraction(s) standardized to acetogenin(s) comprising terminal α,β-unsaturated-γ-methyl-γ-lactone moiety derived from *Annona squamosa*, acetogenin(s) comprising terminal α,β-unsaturated-γ-methyl-γ-lactone moiety include but not limited to squamocin C (LI12103; 1), isosquamocin (LI12132; 2), Dieposabadelin (LI12109; 4), squamostatin D (LI12106; 5), squamocin L (LI12107; 6), squamocin J (LI12111; 7), squamocin G (LI12105; 10), and 10-hydroxyasimicin (LI12110; 11); and compounds that are isolated and sufficiently characterized, which include, compound LI12104 (3), compound LI12114 (8), compound LI12115 (9); and compounds that are isolated but whose structural elucidation is in the process include compound LI12112, compound LI12113, compound LI12116 and compound LI12117.

In another embodiment, the disclosure also provides *Annona squamosa* derived extracts and fractions wherein the concentration of acetogenin(s) comprising terminal α,β-unsaturated-γ-methyl-γ-lactone moiety varies in the range from 0.01% to 50% by weight. In another embodiment, the disclosure also provides *Annona squamosa* derived extracts and fractions wherein the concentration of acetogenin(s) comprising terminal α,β-unsaturated-γ-methyl-γ-lactone moiety varies in the range from 0.01% to 30% by weight.

In another embodiment, the disclosure also provides *Annona squamosa* derived extracts and fractions wherein the concentration of acetogenin(s) comprising terminal α,β-unsaturated-γ-methyl-γ-lactone moiety varies in the range from 0.1% to 10% by weight. In another embodiment, the disclosure also provides the compositions comprising the extract and fractions derived from *Annona squamosa*, wherein the percentage of *Annona squamosa* derived component in the composition varies in the range from 0.01% to 99.9% by weight.

In another embodiment, the disclosure also provides the compositions comprising the extract and fractions derived from *Annona squamosa*, wherein the percentage of *Annona squamosa* derived component in the composition varies in the range from 0.01% to 70% by weight.

In another embodiment, the disclosure also provides the compositions comprising the extract and fractions derived from *Annona squamosa*, wherein the percentage of *Annona squamosa* derived component in the composition varies in the range from 0.1% to 50% by weight.

In another embodiment, the disclosure also provides the compositions comprising the extract and fractions derived from *Annona squamosa*, wherein the percentage of *Annona squamosa* derived component in the composition varies in the range from 0.1% to 30% by weight.

In the other embodiment, disclosure provides extract(s) and fraction(s) standardized to acetogenin(s) derived from the plant parts of *Annona squamosa*, wherein the plants are selected from fruits, leaves, flowers, stem, bark, root, hardwood or mixtures thereof, preferably leaves.

In the other embodiment, disclosure provides extract(s) and fraction(s) standardized to acetogenin(s) wherein the medium for extraction of the plant parts can be selected from hexane, petroleum ether, ethylether, dichloromethane, chloroform, ethyl acetate, acetone, acetonitrile, methanol, ethanol, propanol, n-butanol, iso-propanol, methyl isobutyl ketone and water or mixtures.

In other important embodiment, the disclosure provides a process for the preparation of novel extracts from the plant *Annona squamosa*, which consists of extracting the leaves with an organic solvent or aqueous organic solvent at temperatures ranging from 25 to 80° C., and then extracting spent leaf residue with water at temperatures ranging from 25 to 100° C., and then combining the said extracts together to obtain potent extract containing the acetogenins.

In other important embodiment, the disclosure provides a process for the preparation of extracts from the plant *Annona squamosa*, which consists of extracting the leaves with an organic solvent or aqueous organic solvent at temperatures ranging from 25 to 80° C., and extracting separately the seeds of *Annona squamosa* with an organic solvent or aqueous organic solvent, and then combining the leaf extract and seed extract in therapeutically effective ratio ranging from 9:1 to 2:8 to obtain a novel extract containing acetogenin(s), alternatively, the said leaves and said seeds are mixed together in desired ratio and then extracted with an organic solvent or water or mixtures thereof.

In the other important embodiment, the disclosure provides fractions standardized to acetogenin(s) derived from *Annona squamosa* for the prevention, control and/or treatment of inflammatory, immune or metabolic disorders/disorders as described above, wherein the said acetogenin(s) are obtained using at least one separation technique selected from partition(s), precipitation(s), crystallization, normal phase chromatography, reversed phase chromatography, size exclusion chromatography and ion exchange chromatography or combinations thereof.

In yet another embodiment of the disclosure, the biologically active ingredient(s) used for making the compositions is/are selected from the extracts/fractions/active compounds or phytochemicals having any health benefit selected from anti-inflammatory activity, anti-arthritic activity, anti-diabetic activity, anti-hyperglycemic activity, hypolipidemic activity, anti-obesity activity, anti-hypertensive activity, anti-platelet aggregation activity, anti-infective activity, anti-atherosclerotic activity, anti-oxidant(s) and bio-enhancing activity.

In preferred embodiment, a few biologically active components can be selected from Glucosamine, Glucosamine salts, Chondroitin, Methylsulfonylmethane (MSM), Hyaluronic acid, collagen, polyglycans, Chitosan, Undenatured collagen type-II, SAM-e, omega-3, NEM, quercetin, boron, manganese, calcium ascorbate, flavonoids, alkaloids, phytosterols, terpenes, omega 3 fatty acid(s); extracts or fractions derived from the plant parts of *Withania somnifera, Sphaeranthus indicus, Boswellia serrata, Curcuma longa, Psidium guajava*, pine bark, *Piper nigrum* or *Piper longum*, wherein the plants are selected from fruits, leaves, flowers, stem, bark, root, hardwood or mixtures thereof using hexane, petroleum ether, ethylether, dichloromethane, chloroform, ethyl acetate, acetone, acetonitrile, methanol, ethanol, propanol, n-butanol, iso-propanol, methyl isobutyl ketone, water or mixtures employing conventional techniques.

In another embodiment it is contemplated that the compositions, extracts or fractions comprising acetogenins comprising α,β-unsaturated-γ-methyl-γ-lactone moiety in combination with biologically active ingredients or functional ingredients exhibit synergism.

In still another embodiment, the pharmaceutically or dietetically acceptable excipients, vehicles, diluents and carriers comprises surfactants, binders, disintegrators, lubricants, preservatives, stabilizers, buffers, suspensions and drug delivery systems used for the making the compositions comprise surfactants, binders, diluents, disintegrators, lubricants, preservatives, stabilizers, buffers, suspensions and drug delivery systems, wherein the said pharmaceutically or dietetically acceptable excipients, carriers and diluents comprise glucose, fructose, sucrose, maltose, yellow dextrin, white dextrin, fumed silica, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, preservatives, distilled water, saline, aqueous glucose solution, alcohol, propylene glycol and polyethylene glycol, various animal and vegetable oils, white soft paraffin, paraffin and wax.

In other embodiment of the disclosure, the extract(s) or fraction(s) standardized to acetogenin(s) or their composition(s) derived from *Annona squamosa* can be formulated as oral agents such as tablets, soft capsule, hard capsule, soft gel capsules, pills, granules, powders, emulsions, suspensions, syrups, pellets, food, beverages, concentrated shots, drops and the like; and parenteral agents such as injections, intravenous drip and the like; suppositories; and transdermal agents such as patches, topical creams and gel; ophthalmic agents; nasal agents; and food or beverages.

In other embodiment, the extract(s) or fraction(s) standardized to acetogenin(s) derived from *Annona squamosa* or their composition(s) are administered orally, topically, parenterally or by inhalation to a subject or mammal or warm blooded animal in need thereof.

In other embodiment, the extract(s) or fraction(s) standardized to acetogenin(s) derived from *Annona squamosa* or their composition(s) are administered orally, topically, parenterally or by inhalation to a subject or mammal or warm blooded animal in need thereof, wherein said ingredient or composition(s) are administered once daily or multiple administrations per day or as prescribed by physician/doctor.

In other embodiment of the disclosure, the extract(s) or fraction(s) standardized to acetogenein(s) derived from *Annona squamosa* or their composition(s) are delivered in the form of controlled release tablets, using controlled release polymer-based coatings by the techniques including nanotechnology, microencapsulation, colloidal carrier systems and other drug delivery systems.

In other embodiment of the disclosure, the extract(s) or fraction(s) standardized to acetogenin(s) derived from *Annona squamosa* or their composition(s) can be formulated into or added to existing or new food and beverage form(s) as a healthy food for warm blooded animals.

In another embodiment, the disclosure relates to the use of the extract(s) or fraction(s) standardized to acetogenein(s) derived from *Annona squamosa* or their composition(s) in preparation of various pharmaceutical dosage forms, dietary supplements, food ingredients and beverages.

In other important embodiment, the disclosure provides a method of modulation of the expression or production of atleast one biomarker selected from PPAR-γ, C-reactive protein (CRP), Adipose Differentiation Related Protein (ADRP), CEBPα, CEBP1β, adipocyte CD36, macrophage CD36, Monocyte Chemotactic protein (MCP-1), Oxidized LDL, Adipocyte Fatty-acid-Binding Protein (aP2/FABP4/A-FABP), Beta-3 adrenergic receptor (β3-AR), adiponectin, Perilipin, Protein tyrosine phosphatase 1B (PTP 1B), Matrix Metalloproteinase-1 (MMP-1), Matrix Metalloproteinase-3 (MMP-3) and Matrix Metalloproteinase-13 (MMP-13) in a subject or mammal or warm blooded animal in need thereof, wherein the method comprises supplementing the said subject or warm blooded animals or mammal with an effective dose of an extract or fraction standardized to acetogenin(s) or mixtures thereof derived from *Annona squamosa* or their composition.

In other important embodiment, the disclosure provides a method of inhibiting adipogenesis and/or accelerating lipolysis in a mammal, wherein the method comprises supplementing the said mammal with an effective dose of an extract or fraction standardized to acetogenin(s) or mixtures thereof derived from *Annona squamosa* or their composition.

In other embodiment, the extract(s) or fraction(s) standardized to acetogenein(s) derived from *Annona squamosa* or their composition(s) can be administered in any therapeutically effective dosage for benefits such as amelioration of symptoms, slowing of disease progression or prevention of disease such as in a range from 0.01 to 250 mg/kg body weight/day, preferably in the range from 0.1 to 50 mg/kg body weight/day.

In a further embodiment, the current disclosure provides the process for producing extracts and fractions comprising novel acetogenin compositions, acetogenin compositions and also pure acetogenin compounds from *Annona squamosa* leaf.

The other embodiments of the current disclosure further provide the usage of the extract(s) or fraction(s) standardized to acetogenein(s) derived from *Annona squamosa* or their composition(s) as it is or in comminuted form and/or in unmodified form as granules, powder, precipitate, extract, dried extract and/or exudates, or the active ingredients are formulated into a solid, semi-solid or liquid dosage form by adding a conventional biologically or pharmaceutically acceptable salt(s) or additive(s).

In a further embodiment, the disclosure provides that therapeutically effective amount of the extract(s) or fraction(s) standardized to acetogenein(s) derived from *Annona squamosa* or their composition(s) can be administered in a specific dosage form such as orally, topically, transdermally, parenterally or in the form of a kit to a subject or patient in need thereof.

In accordance to the current disclosure, the compositions of the current disclosure can be formulated into any dietary supplement, food and beverage forms for human and animal applications.

In another embodiment, the disclosure further comprises, mixing the compositions of the current disclosure with various components used in the animal feed for the purpose of curing, preventing or treating inflammation/immune associated or related diseases and/or for treating metabolic disorders.

The following examples, which include preferred embodiments, will serve to illustrate the practice of this disclosure, it being understood that the particulars shown are by way of example and for purpose of illustrative discussion of preferred embodiments of the disclosure and they are not to limit the scope of the disclosure.

Example 1

Preparation of Methanol Extract (LI12100) of the Leaves of *Annona squamosa*

Dried leaves of the plant material *Annona squamosa* (1.1 Kg) were pulverized to coarse powder and charged into a pilot extractor and extracted with methanol (6.6 L) at 60-65° C. temperature for 2 h. The extract was filtered and the spent raw material was re-extracted twice with methanol (2×5.5 L) under similar conditions. The combined extract was fine filtered and concentrated under vacuum to obtain methanol extract as a dark colored residue (LI12100; 150 g; 0.4% squamocin C).

Example 2

Preparation of Hexane Extract (LI12100A), Ethyl Acetate Extract (LI12101) and Methanol Extract (LI12100B) of the Leaves of *Annona squamosa*

Dried leaves of the plant material *Annona squamosa* (2 Kg) were pulverized to coarse powder and charged into a pilot extractor and extracted with water (14 L) at ambient temperature. The extract was filtered and the spent raw material was dried under shade. The dried spent raw material was extracted successively with cold hexane (14 L) at 10-15° C. for 2 h, followed by ethyl acetate (3×12 L) at reflux temperature for 2 h per extraction and finally with methanol (2×6 L) at 65° C. for 2 h per extraction. The extracts were fine filtered and concentrated separately under vacuum to obtain hexane extract (LI12100A; 58 g), ethyl acetate extract (LI12101; 160 g; 0.5% squamocin C) and methanol extract (LI12100B; 150 g).

Example 3

Preparation of Ethyl Acetate Extract (LI12100C) of the Leaves of *Annona squamosa*

Dried leaves of the plant material *Annona squamosa* (1 Kg) were pulverized to coarse powder and charged into a pilot extractor and extracted with ethyl acetate (6 L) at reflux temperature for 2 h. The extract was filtered and the spent raw material was re-extracted twice with ethyl acetate (2×6 L) under similar conditions. The combined extract was fine filtered and concentrated under vacuum to obtain a residue (LI12100C; 99 g).

Example 4

Preparation of Ethanol Extract (LI12100D) of the Leaves of *Annona squamosa*

Dried leaves of the plant material *Annona squamosa* (1 Kg) were pulverized to coarse powder and charged into a pilot extractor and extracted with ethanol (6 L) at 65-70° C. temperature for 2 h. The extract was filtered and the spent raw material was re-extracted twice with ethyl alcohol (2×5 L) under similar conditions. The combined extract was fine filtered and concentrated under vacuum to obtain ethanol extract as a dark colored residue (LI12100D; 132 g).

Example 5

Preparation of Hydroalcohol (60% Ethanol) Extract (LI12100E) of the Leaves of *Annona squamosa*

Dried leaves of the plant material *Annona squamosa* (1 Kg) were pulverized to coarse powder and charged into a pilot extractor and extracted with 60% ethanol (6 L) at 65-70° C. temperature for 2 h. The extract was filtered and the spent raw material was re-extracted twice with 60% ethanol (2×5 L) under similar conditions. The combined extract was fine filtered and concentrated under vacuum to obtain hydroalcohol extract as a dark colored residue (LI12100E; 120 g).

Example 6

Preparation of Ethyl Acetate Partitioned Extract (LI12100F) of Leaves of *Annona squamosa*

The ethanol extract (25 g) as obtained in example 4 was portioned between water (200 mL) and ethyl acetate (200 mL). The organic layer was separated, dried over sodium sulfate and evaporated under vacuum to obtain a residue (LI12100F, 19 g).

Example 7

Preparation of Hexane Extract (LI12100G) of the Seeds of *Annona squamosa*

Dried seeds of *Annona squamosa* (300 g) were pulverized to coarse powder and extracted with hexane (1.2 L) at reflux for 2 h. The extract was filtered and the spent raw material was re-extracted twice with hexane (2×1 L) under similar conditions. The combined extract was fine filtered and concentrated under vacuum to obtain hexane extract (LI12100G; 27 g) of the seeds.

Example 8

Preparation of Ethyl Acetate Extract (LI12100H) of the Seeds of *Annona squamosa*

Dried seeds of *Annona squamosa* (300 g) were pulverized to coarse powder and extracted with ethyl acetate (1.2 L) at reflux for 2 h. The extract was filtered and the spent raw material was re-extracted twice with ethyl acetate (2×1 L) under similar conditions. The combined extract was fine filtered and concentrated under vacuum to obtain ethyl acetate extract (LI12100H; 27 g).

Example 9

Preparation of Novel Extract of the Leaves of *Annona squamosa* (LI12100I)

Dried leaves of the plant material *Annona squamosa* (1 Kg) were pulverized to coarse powder and charged into a pilot extractor and extracted with methanol (6 L) at 60-65° C. temperature for 2 h. The extract was filtered and the spent raw material was re-extracted twice with methyl alcohol (2×5 L) under similar conditions. The combined extract was fine filtered and concentrated under vacuum to obtain methanol extract as a dark colored residue (LI12100; 124 g). The spent raw material was then shade dried and the spent residue (800 g) was extracted with water (6 L) at 65-70° C. for 1 h. The extract was filtered and the spent raw material was extracted one more time with water. The combined water extract was fine filtered and concentrated under vacuum to obtain the water extract (85 g). The methanol extract and the water extract were blended properly and sieved through 40 mesh to obtain the novel extract (LI12100I; 203 g) of the leaves of *Annona squamosa*.

Example 10

Preparation of Novel Extract of the Seeds and Leaves of *Annona squamosa* (LI12100J)

A raw material blend containing 800 g of dried leaves and 200 g of dried seeds of *Annona squamosa* were pulverized to a coarse powder and charged into a pilot extractor and extracted with methanol (6 L) at 60-65° C. temperature for 2 h. The extract was filtered and the spent raw material was re-extracted twice with methyl alcohol (2×5 L) under similar conditions. The combined extract was fine filtered and concentrated under vacuum to obtain methanol extract of the blend as a dark colored residue (LI12100J; 124 g).

Example 11

Compositions Derived from *Annona squamosa*

1) Composition-1A: Composition-1A was prepared by mixing unit doses of the following components; Two parts of *Annona squamosa* leaf methanol extract (LI12100) (2 g) and one part of *Boswellia serrata* low polar gum resin extract (BsLPRE) (1 g).

2) Composition-1B: Composition-1B was prepared by mixing unit doses of the following components; one part of *Annona squamosa* leaf methanol extract (LI12100) (2 g) and one part of *Boswellia serrata* low polar gum resin extract (BsLPRE) (2 g).

3) Composition-2A: Composition-2A was prepared by mixing unit doses of the following components; one part of *Annona squamosa* leaf methanol extract (LI12100) (1 g) and two parts of *Boswellia serrata* extract standardized to 85% total Boswellic acids (BSE 85%) (2 g).

4) Composition-2B: Composition-2B was prepared by mixing unit doses of the following components; one part of *Annona squamosa* leaf methanol extract (LI12100) (1 g) and three parts of *Boswellia serrata* extract standardized to 85% total Boswellic acids (BSE 85%) (3 g).

5) Composition-3A: Composition-3A was prepared by mixing unit doses of the following components; one part of *Annona squamosa* leaf methanol extract (LI12100) (1 g) and two parts of *Psidium guajava* leaf methanol extract (2 g).

6) Composition-3B: Composition-3B was prepared by mixing unit doses of the following components; Two parts of *Annona squamosa* extract (LI12100) (2 g) and two parts of *Psidium guajava* leaf methanol extract (2 g).

7) Composition-4A: Composition-4A was prepared by mixing unit doses of the following components; One part of *Annona squamosa* leaf methanol extract (LI12100) (2 g) and one part of calcium ascorbate (2 g).

8) Composition-4B: Composition-4B was prepared by mixing unit doses of the following components; One part of *Annona squamosa* leaf methanol extract (LI12100) (2 g) and two parts of calcium ascorbate (4 g).

9) Composition-5A: Composition-5A was prepared by mixing unit doses of the following components; one part of *Annona squamosa* leaf methanol extract (LI12100) (2 g) and one part of Omega 3 fatty acid (2 g).

10) Composition-5B: Composition-5B was prepared by mixing unit doses of the following components; one part of *Annona squamosa* extract (LI12100) (2 g) and two parts of Omega 3 fatty acid (4 g).

11) Composition-6A: Composition-6A was prepared by mixing unit doses of the following components; one part of *Annona squamosa* leaf methanol extract (LI12100) (2 g) and one part of *Boswellia serrata* extract enriched with 30% of 3-O-acetyl-11-keto-β-Boswellic acid (AKBA) (2 g).

12) Composition-6B: Composition-6B was prepared by mixing unit doses of the following components; one part of *Annona squamosa* leaf methanol extract (LI12100) (2 g) and one part of *Boswellia serrata* extract enriched with 20% of 3-O-acetyl-11-keto-β-Boswellic acid (AKBA) (2 g).

13) Composition-7A: Composition-7A was prepared by mixing unit doses of the following components; one part of *Annona squamosa* leaf methanol extract (LI12100) (2 g) and two parts of *Curcuma longa* extract enriched with 95% of total curcuminoids (4 g).

14) Composition-7B: Composition-7B was prepared by mixing unit doses of the following components; one part of *Annona squamosa* leaf methanol extract (LI12100) (2 g) and four parts of *Curcuma longa* extract enriched with 20% of total curcuminoids (8 g).

15) Composition-8A: Composition-8A was prepared by mixing unit doses of the following components; one part of *Annona squamosa* leaf methanol extract (LI12100) (2 g) and three parts of Glucosamine hydrochloride (6 g).

16) Composition-8B: Composition-8B was prepared by mixing unit doses of the following components; one part of *Annona squamosa* leaf methanol extract (LI12100) (2 g) and five parts of *Curcuma longa* extract enriched with 20% of total curcuminoids (10 g).

17) Composition-9A: Composition-9A was prepared by mixing unit doses of the following components; one part of *Annona squamosa* leaf methanol extract (LI12100) (2 g), one part of *Boswellia serrata* extract (>10% AKBA) (2 g), two parts of *Curcuma longa* extract standardized 95% total curcuminoids(4 g), and one part of Bromelain (2 g).

18) Composition-9B: Composition-9B was prepared by mixing unit doses of the following components; one part of *Annona squamosa* leaf methanol extract (LI12100) (2 g), one part of *Boswellia serrata* extract (>10% AKBA) (2 g), three parts of *Curcuma longa* extract standardized 95% total curcuminoids (6 g), and two parts of Bromelain (4 g).

19) Composition-10A: Composition-10A was prepared by mixing unit doses of the following components; one part of *Annona squamosa* leaf methanol extract (LI12100) (2 g) and one part of *Annona squamosa* seed ethyl acetate extract (LI12100H) (2 g).

20) Composition-10B: Composition-10A was prepared by mixing unit doses of the following components; Four parts of *Annona squamosa* leaf methanol extract (LI12100B) (4 g) and one part of *Annona squamosa* seed ethyl acetate extract (LI12100H) (1 g).

Example 12

Preparation of Active Fractions and Identification of Active Compounds Using Bioassay (Anti-TNFα) Guided Purification The methanol extract (LI12100; 150 gm; $IC_{50}$ 20.06 ng/mL) of *Annona squamosa* leaves was subjected to silica flash column chromatography using ethylacetate/hexane mixtures as eluants. The fractions eluted with 60% and 80% ethyl acetate in hexane (5.2 g and 4.2 respectively) and fraction (8 g) eluted with ethyl acetate have shown potent anti-TNFα activity. The fraction (LI189/159G+H) eluted with ethyl acetate has however shown superior activity ($IC_{50}$ 0.82 ng/mL). A small sample (3 g) of this fraction was subjected to further purification on silica flash column again using acetone/chloroform mixtures. The active compounds have eluted into a fraction (380 mg; 76.6% inhibition at 0.4 ng) eluted with 30% acetone/chloroform. This was further purified on HPLC using 95: 5 acetonitrile/water mixture on a preparative reversed phase silica column (Phenomenex Luna 10μ, C18, 250 mm×21.2) to obtain a fraction (115 mg) having most potent activity. It was again subjected to further purification on HPLC (Phenomenex Luna 10μ, C18, 250 mm×21.2; 90:10 acetonitrile/water mixture) to obtain a pure compound (LI12103, 88 mg) having an $IC_{50}$ value of 24.9 pg/mL. Careful analysis of its spectral data ($^1$H NMR, $^{13}$C NMR and Mass) revealed its identity as squamocin C (LI12103; 1). A minor compound with 63% inhibition at 100 pg/mL was also isolated from the HPLC purifications and its structure is identified as isosquamocin (LI12132; 2, 28 mg). The bioassay guided fractionation is summarized in FIG. 1.

Example 13

Isolation of Acetogenins Containing Terminal α,β-Unsaturated-γ-Methyl-γ-Lactone Moiety and Tetrahydrofuran and/or Epoxide Moieties Using Bioassay Guided Fractionation of Ethyl Acetate Extract (LI12101) of *Annona squamosa*

The extract (LI12101) of *Annona squamosa* (300 g), which showed an $IC_{50}$ value of 8.38 ng/mL against LPS induced TNF a in THP-1 human monocytes cells, was subjected to bio-assay guided column chromatography on silica column using hexane and acetone/hexane mixtures. The fractions eluted with 5% to 40% acetone/hexane mixtures show potential TNFα inhibition. The fraction eluted with 5% acetone/hexane mixture was subjected to repeated chromatography on silica gel first using acetone/hexane mixtures followed by further chromatography of the active fractions obtained on elution with 15-20% acetone/hexane mixtures using ethyl acetate/hexane mixture to obtain LI12104 (3, 250 mg). The fraction on elution of the main column with 10% acetone/hexane on further purification over silica using acetone/hexane mixtures yielded dieposabadelin (LI12109, 4, 150 mg). The fraction obtained on elution of the main column with 20% and 30% acetone/hexane mixtures on repeated purification over silica using acetone/hexane mixtures yielded squamostatin D (LI12106; 5, 40 mg), squamocin L (LI12107; 6, 175 mg), squamocin J (LI12111; 7, 70 mg), compound LI12112 (40 mg), compound LI12113 (46 mg), compound LI12114 (8, 30 mg), compound LI12115 (9, 35 mg) and squamocin G (LI12105; 10, 45 mg), compound LI12116 (17 mg), compound LI12117 (15 mg). The fraction eluted with 40% acetone/hexane yielded on repeated purification over silica using acetone/hexane and ethyl acetate/hexane mixtures yielded squamocin C (LI12103; 1, 1.4 g), isosquamocin (LI12132; 2, 21 mg), 10-hydroxyasimicin (LI12110; 11, 40 mg). The structures of squamocin C, squamocin G, squamostatin D, squamocin L, Dieposabadelin, 10-hydroxyasimicin and squamocin J are confirmed by a comparison of the spectral data with that reported in the literature. The structures of compounds LI12104 (3) and LI12114 (8) are tentatively assigned and the structure identification/confirmation of other compounds is in progress. The extracts and all the chromatographic fractions were monitored for TNFα inhibition using the experimental procedure illustrated in the following example. The isolation of other compounds is in progress.

The NMR and mass spectral data of the acetogenin compounds is summarized below:

LI12103 (squamocin C; 1): 1H NMR (CDCl3, 400 MHz): δ 6.98 (1H, d, J=1.5 Hz), 4.98 (1H, m), 3.94-3.80 (5H, m), 3.62-3.55 (1H, m), 3.41-3.37 (1H, m), 2.26 (2H, t, J=7.2 Hz), 2.06-1.79 (m), 1.40 (3H, d, J=6.8 Hz), 1.68-1.25 (m), 0.88 (3H, t, J=6.8 Hz); 13C NMR (CDCl3, 100 MHz): δ 173.8, 148.7, 134.3, 83.3, 82.8, 82.4, 82.1, 77.1, 74.1, 71.8, 71.6, 37.5, 37.3, 33.8, 33.4, 32.6, 31.9, 31.8, 29.7-29.2, 28.9, 28.4, 27.4, 25.6, 25.2, 24.9, 22.7, 22.6, 22.0, 19.2, 14.0; LCMS: m/z 645 (M+Na)$^+$,+ve ion mode.

LI12132 (isosquamocin; 2): $^1$H NMR (CDCl$_3$, 400 MHz): δ 6.99 (1H, s), 4.99 (1H, q, J=6.4 Hz), 3.94-3.84 (5H, m), 3.58 (1H, m), 3.39 (1H, m), 2.26 (2H, t, J=7.6 Hz), 1.98-1.80 (m), 1.62-1.52 (m), 1.40 (3H, d, J=6.8 Hz), 1.68-1.25 (m), 0.88 (3H, t, J=6.8 Hz); $^{13}$C NMR (CDCl$_3$, 100 MHz): δ 173.8, 148.8, 134.3, 83.3, 82.8, 82.5, 82.2, 77.6, 74.1, 71.7, 71.3, 37.4, 37.2, 33.1, 32.4, 31.9, 31.8, 29.7-29.2, 28.9, 27.3, 25.6, 25.1, 24.7, 22.6, 21.9, 19.2, 14.0; LCMS: m/z 645 (M+Na)$^+$, +ve ion mode.

LI12104 (3): 1H NMR (CDCl3, 400 MHz): δ 6.98 (1H, d, J=1.6 Hz), 5.40 (2H, m), 4.99 (1H, qd, J=6.8, 1.6 Hz), 2.97 (4H, m), 2.24 (4H, m), 2.25 (2H, m), 1.77 (2H, m), 1.69 (2H, m), 1.63-1.47 (10H, m), 1.40 (3H, d, J=6.8 Hz), 1.26 (s), 0.88 (3H, t, J=6.8 Hz); 13C NMR (CDCl3, 100 MHz): δ 173.8, 148.7, 134.4, 131.1, 128.1, 57.3, 56.9, 56.8, 56.7, 56.4, 31.9, 29.6, 29.6, 29.5, 29.5, 29.3, 29.3, 29.2, 27.9, 27.8, 27.8, 27.4, 27.2, 26.6, 25.7, 25.3, 25.2, 25.1, 24.9, 24.3, 22.6, 19.2, 14.0; LCMS: 595 (M+Na)$^+$+ve ion mode.

LI12109 (dieposabadelin; 4): 1H NMR (CDCl3, 400 MHz): δ 6.98 (1H, s), 4.99 (1H, qd, J=6.4, 1.6 Hz), 2.94 (4H, s), 2.27 (2H, t, J=8.0 Hz), 1.77 (2H, m), 1.63 (2H, m), 1.57-1.44 (10H, m), 1.40 (3H, d, J=6.8 Hz), 1.26 (s), 0.88 (3H, t, J=6.8 Hz); 13C NMR (CDCl3, 100 MHz): δ 173.7, 148.7, 134.4, 57.3, 56.7, 34.1, 31.9, 29.6, 29.6, 29.3, 29.2, 27.8, 27.4, 26.6, 25.2, 25.2, 22.6, 19.2, 14.0; LCMS: 569 (M+Na)$^+$+ve ion mode.

LI12106 (squamostatin D; 5): 1H NMR (CDCl3, 400 MHz): δ 6.98 (1H, d, J=1.6 Hz), 4.99 (1H, qd, J=6.8, 1.6 Hz), 3.90-3.85 (2H, m), 3.83-3.78 (3H, m), 3.41 (2H, m), 2.71 (1H, s), 2.26 (2H, t, J=8.4 Hz), 2.04-1.97 (4H, m), 1.95-1.85 (2H, m), 1.73-1.68 (4H, m), 1.55-1.44 (8H, m), 1.41 (3H, d, J=6.8 Hz), 1.28 (s), 0.88 (t, J=6.8 Hz); LCMS: 645 (M+Na)$^+$+ve ion mode.

LI12107 (squamocin L; 6): 1H NMR (CDCl3, 400 MHz): δ 6.98 (1H, d, J=1.6 Hz), 4.99 (1H, qd, J=6.8, 2.0 Hz), 3.94-3.91 (2H, m), 3.89-3.84 (3H, m), 3.39 (1H, m), 2.49 (1H, br s), 2.26 (2H, t, J=8.4 Hz), 2.18 (1H, s), 1.98 (4H, m), 1.94-1.79 (2H, m), 1.67-1.51 (8H, m), 1.41 (3H, d, J=6.8 Hz), 1.26 (s), 0.88 (3H, t, J=6.8 Hz); 13C NMR (CDCl3, 100 MHz): δ 173.8, 148.8, 134.4, 83.2, 82.8, 82.4, 82.2, 77.2, 74.1, 71.5, 33.5, 32.5, 31.9, 29.7, 29.6, 29.5, 29.5, 29.3, 29.2, 28.9, 28.8, 28.3, 27.4, 26.0, 25.7, 25.2, 24.6, 22.6, 19.2, 14.1; LCMS: 629 (M+Na)$^+$+ve ion mode.

LI12111 (squamocin J; 7): 1H NMR (CDCl3, 400 MHz): δ 6.98 (1H, d, J=1.6 Hz), 4.99 (1H, qd, J=6.8, 1.6 Hz), 3.95-3.82 (5H, m), 3.39 (1H, m), 2.49 (1H, s), 2.43 (1H, s), 2.26 (2H, t, J=8.4 Hz), 2.18 (1H, s), 2.01-1.96 (5H, m), 1.94-1.81 (2H, m), 1.72-1.51 (8H, m), 1.41 (3H, d, J=6.8 Hz), 1.26 (s), 0.88 (3H, t, J=6.8 Hz); 13C NMR (CDCl3, 100 MHz): δ 173.8, 148.7, 134.4, 83.1, 82.8, 82.2, 77.2, 74.1, 71.5, 33.5, 32.5, 31.9, 29.7, 29.7, 29.6, 29.5, 29.5, 29.3, 29.2, 28.9, 28.8, 28.4, 27.4, 26.0, 25.6, 25.2, 24.6, 22.6 19.2, 14.0; LCMS: 601 (M+Na)$^+$+ve ion mode.

LI12114 (8): 1H NMR (CDCl3, 400 MHz): δ 6.98 (1H, d, J=1.6 Hz), 4.99 (1H, qd, J=6.8, 1.6 Hz), 3.87 (5H, m), 3.37 (1H, m), 2.52 (1H, br s), 2.26 (2H, t, J=7.2 Hz), 1.98-1.93 (5H, m), 1.76-1.45 (10H, m), 1.41 (3H, d, J=6.8 Hz), 1.26 (s), 0.88 (3H, t, J=6.8 Hz); 13C NMR (CDCl3, 100 MHz): δ 173.8, 148.7, 134.4, 83.1, 82.2, 82.1, 81.0, 80.9, 79.8, 74.3, 74.1, 74.1, 35.8, 33.6, 32.1, 31.8, 29.7, 29.6, 29.4, 29.3, 29.2, 29.1, 28.7, 28.4, 28.3, 28.1, 27.9, 27.8, 27.7, 27.4, 27.2, 26.1, 25.6, 25.2, 22.6, 19.2, 14.0; LCMS: 627 (M+Na)$^+$+ve ion mode.

LI12115 (9): 1H NMR (CDCl3, 400 MHz): δ 6.98 (1H, d, J=1.6 Hz), 4.99 (1H, qd, J=6.8, 1.6 Hz), 3.95-3.82 (4H, m), 3.39 (1H, m), 2.26 (2H, t, J=8.4 Hz), 2.04-1.92 (5H, m), 1.67-1.60 (8H, m), 1.58-1.49 (5H, m) 1.41 (3H, d, J=6.8 Hz), 1.26 (s), 0.88 (3H, t, J=6.8 Hz); 13C NMR (CDCl3, 100 MHz): δ 173.8, 148.8, 134.4, 83.0, 82.9, 82.0, 81.2, 79.9, 77.2, 74.1, 35.9, 33.5, 32.1, 31.9, 29.7, 29.7, 29.6, 29.5, 29.5, 29.3, 29.2, 28.9, 28.8, 28.4, 27.4, 26.1, 25.7, 25.2, 22.7, 19.2, 14.1; 562 (M+Na)$^+$+ve ion mode.

LI12105 (squamocin G; 10): 1H NMR (CDCl3, 400 MHz): δ 7.18 (1H, d, J=1.2 Hz), 5.05 (1H, dq, J=1.2, 6.8 Hz), 3.95-3.81 (6H, m), 3.41-3.37 (1H, m), 2.51 (1H, td, J=1.6, 14.8 Hz), 2.42 (1H, dd, J=8.4, 15.2 Hz), 2.24 (m), 2.01-1.79 (m), 1.66-1.61 (4H, m), 1.43 (3H, d, J=6.8 Hz), 1.25-1.49 (m), 0.88 (3H, t, J=6.8 Hz); 13C NMR (CDCl3, 100 MHz): δ 174.5, 151.7, 131.3, 83.2, 82.8, 82.4, 82.2, 77.9, 74.1, 71.5, 70.1, 37.5, 33.5, 33.4, 32.6, 31.9, 29.7-28.9, 28.4, 26.1, 25.7, 25.6, 24.7, 22.7, 19.1, 14.1. LCMS: nth 645 (M+Na)$^+$,+ve ion mode.

LI12110 (10-hydroxyasimicin; 11): 1H NMR (CDCl3, 400 MHz): δ 6.98 (1H, d, J=1.6 Hz), 4.99 (1H, qd, J=6.8, 1.6 Hz), 3.90-3.77 (5H, m), 3.60 (1H, br s), 3.41 (2H, m), 2.75 (2H, dd, J=2.8, 5.6 Hz), 2.26 (2H, tt, J=1.6, 7.6 Hz), 2.16 (1H, br s), 2.03-1.84 (4H, m), 1.72-1.50 (13H, m), 1.41 (3H, d, J=6.8 Hz), 1.28 (s), 0.88 (3H, t, J=7.2 Hz); 13C NMR (CDCl3, 100 MHz): δ 173.8, 148.8, 134.4, 83.3, 82.2, 81.9, 79.4, 77.3, 76.9, 76.7, 74.5, 74.5, 71.8, 71.7, 37.5, 37.3, 35.6, 32.6, 32.4, 31.8, 29.7, 29.7, 29.6, 29.5, 29.4, 29.3, 29.3, 29.1, 28.6, 28.4, 27.4, 26.2, 25.6, 25.5, 25.2, 22.6, 21.9, 19.2, 14.0; LCMS: 661 (M+Na)$^+$+ve ion mode.

LI12112: $^1$H NMR (CDCl$_3$, 400 MHz): δ 6.98 (1H, d, J=1.2 Hz), 5.36 (2H, m), 4.99 (1H, qd, J=1.6, 6.8 Hz), 3.87 (4H, m), 3.41 (2H, m), 2.36-2.24 (4H, m), 2.06-1.90 (5H, m), 1.68-1.50 (8H, m), 1.41 (3H, d, J=6.8 Hz), 1.25 (s), 0.88 (3H, t, J=6.8 Hz); LCMS: 629 (M+Na)$^+$+ve ion mode.

LI12113: 1H NMR (CDCl3, 400 MHz): δ 6.98 (1H, d, J=1.6 Hz), 4.99 (1H, qd, J=1.6, 6.8 Hz), 3.03-2.92 (6H, m), 2.26 (2H, t, J=7.6 Hz), 2.04-1.95 (2H, m), 1.84 (2H, m), 1.78 (2H, m), 1.66-1.47 (10H, m), 1.40 (3H, d, J=6.8 Hz), 1.26 (s), 0.88 (3H, t, J=6.8 Hz); 13C NMR (CDCl3, 100 MHz): δ 173.7, 148.7, 138.4, 57.3, 56.8, 56.6, 31.9, 29.7, 29.5, 29.5, 29.3, 29.2, 27.8, 27.4, 26.6, 25.3, 25.2, 25.2, 22.6, 19.2, 14.1; LCMS: 611 (M+Na)$^+$+ve ion mode.

LI12116: 1H NMR (CDCl3, 400 MHz): δ 6.98 (1H, s), 4.99 (1H, qd, J=6.4, 1.6 Hz), 4.29 (1H, m) 2.98 (4H, m), 2.27 (2H, t, J=8.0 Hz), 2.07 (2H, m), 1.77 (6H, m), 1.55 (10H, m), 1.41 (3H, d, J=6.8 Hz), 1.26 (s), 0.88 (3H, t, J=6.8 Hz); LCMS: 627 (M+Na)$^+$+ve ion mode.

LI12117: 1H NMR (CDCl3, 400 MHz): δ 6.98 (1H, d, J=1.2 Hz), 5.35 (2H, m) 4.98 (1H, qd, J=6.8, 1.6 Hz), 4.16 (1H, m), 3.93-3.82 (4H, m), 3.56 (1H, m), 3.40 (1H, m), 2.29 (3H, m), 2.06 (4H, m), 1.67-1.50 (16H, m), 1.40 (3H, d, J=6.8 Hz), 1.26 (s), 0.88 (3H, t, J=6.8 Hz); LCMS: 643 (M+Na)$^+$+ve ion mode.

Example 14

Inhibition of Tumor necrosis factor-α (TNF-α) in vitro by extracts, fractions and compounds of *Annona squamosa*: The anti-inflammatory activities of extracts, fractions and compounds of *Annona squamosa* were assessed in a cell based in vitro assay. Briefly, THP-1 human monocytes cells were washed and re-suspended in phenol red free Dulbecco's Modified Eagle's Medium (DMEM) supplemented with 1% fetal Bovine serum (FBS). Equal number of cells was added to each well of a 96-well TC plate and the cells were pretreated for 2 h with various concentrations (ranging from 0.1 to 200 ng/mL; solutions prepared in culture medium from a stock solution containing 50 mg/l mL DMSO of each test compound) of extracts, fractions and compounds of *Annona squamosa*. The inflammatory response was induced by 100 ng/mL of LPS for 4 h at 37° C. in presence of 5% CO$_2$. The vehicle control culture wells received 0.1% DMSO in culture medium. The cell culture supernatants were collected and assessed for secretory pro-inflammatory cytokine, TNFα. The TNFα concentration was quantitatively measured by highly specific and sensitive Enzyme Immuno Assay (EIA) kit supplied by R&D Systems, USA. The enzyme immuno assay was performed based on the protocol provided by the vendor. The inhibitory concentration for 50% inhibition (IC$_{50}$) of TNFα was determined from a plot drawn for ingredient concentrations against corresponding TNFα levels. The IC$_{50}$ value for *Annona squamosa* extract LI12101 was found to be 8.4 ng/mL. Table 1 is a summary of 50% inhibitory (IC$_{50}$) concentrations of various extracts, fractions and compounds derived from *Annona squamosa* plant parts in cell based in vitro model.

TABLE 1

| Compound code or name | TNFα inhibition IC$_{50}$ (ng/ml) |
|---|---|
| LI12100 | 20.4 |
| LI12101 | 8.38 |
| LI12100A | 45.28 |
| LI12100B | 93.31 |
| LI12100C | 15.29 |
| LI12100D | 29.16 |
| LI12100E | 104.38 |
| LI12100G | 3.1 |
| LI12100H | 2.3 |
| Squamocin C | 0.0249 |
| LI12104 | >5 |
| Squamocin G | 0.124 |
| Squamostatin D | 4.08 |
| Squamocin L | 0.116 |
| Dieposabadelin | >5 |
| 10-Hydroxyasimicin | 3.21 |
| Isosquamocin | 0.080 |
| LI12112 | 3.68 |

Example 15

Inhibition of Matrix Metalloproteinase-3 (MMP-3) Production by the Extracts and Fractions Derived from the Leaves of *Annona squamosa*

Inhibition of matrix metalloproteinase-3 production by *Annona squamosa* extract (LI12100) was evaluated in Interleukin-1β induced human lung tumor cell line A549. Briefly, the cells were cultured in DMEM with 2 mM Glutamine, 100 U/mL penicillin, 100 μg/mL streptomycin and 10% fetal bovine serum (Hyclone, Logan, Utah). Five thousand cells per well were seeded into a 96-well cell culture plate (Corning, USA) one day before the experiment. The culture media was replaced with fresh DMEM containing 10% fetal bovine serum. LI12100 extract serially diluted in medium, ranging from 0.1 to 10 μg/mL was pre-incubated with cells for 2 hour at 5% CO2 at 37° C., and then stimulated with 10 ng/mL human IL-1β (R&D System, Minneapolis, Minn.) for 24 hours. The supernatant was harvested and used to measure MMP3 production by ELISA development kit (R&D System, Minneapolis, Minn., USA). The MMP3 concentration in culture supernatant was estimated quantitatively by interpolating the optical densities into the standard curve generated from known concentrations of MMP3. The percentage inhibition obtained at 10 μg/mL concentration for different extracts of *Annona squamosa* is summarized in Table 2.

TABLE 2

| Compound code or name | MMP3 % inhibition @ 10 μg/mL |
|---|---|
| LI12101 | 42.0 |
| LI12100A | 37.8 |
| LI12100B | 30.7 |
| LI12100C | 24.6 |
| LI12100D | 30.7 |

Example 16

In Vivo Anti-Inflammatory Activity of *Annona squamosa* Extract (LI12101) Comprising Acetogenin Composition The in vivo anti-inflammatory efficacy of *Annona squamosa* ethyl acetate extract (LI12101; 0.2% squamocin C) comprising acetogenin composition was evaluated in Freund's Complete Adjuvant induced arthritis model of Sprague Dawley rats. The rats of either sex were randomly selected and divided into two groups comprising 5 animals in each group. The treatment group rats were supplemented with 100 mg/kg body weight of *Annona squamosa* extract (LI12101) or 10 mg/kg body weight of prednisolone per day for 14 days. All the supplements were diluted in 10 mL of 0.5% CMC. The control group of animals was supplemented with same volume (10 mL) of 0.5% CMC. Prednisolone was administered as positive control. On the 14$^{th}$ day, Freund's Complete Adjuvant (FCA) was subcutaneously injected in the sub-plantar region of the left hind paw of each animal. The experiment was terminated 13 days after FCA inoculation. At the end of the experiment, the animals were sacrificed, the liver tissue samples excised and stored at −80° C. Blood samples were collected from each animal at regular intervals and paw volumes were measured on the day of FCA injection and after 13 days of FCA inoculation. The difference in paw edema volume at the day of FCA injection and at 13$^{th}$ day after FCA inoculation is considered as the inflammatory response for the supplement. The in vivo anti-inflammatory responses of *Annona squamosa* extract (LI12101) and prednisolone were estimated by calculating the percentage inhibition of paw edema when compared to the paw edema observed in the CMC supplemented control group. The data is summarized in FIG. 3.

The treatment group supplemented with *Annona squamosa* extract (LI12101) exhibited 65% reduction in paw volume compared to 71% reduction shown by the positive control prednisolone. The levels of cytokine tumor necrosis factor alpha (TNFα) were evaluated in blood serum collected 13 days after FCA challenge. The serum cytokine levels were measured using enzyme-immune assay kit supplied by R & D systems, USA. The treatment groups supplemented with LI12101 and prednisolone showed significant reduction in serum cytokine levels (TNFα) as depicted in FIG. 4.

Example 17

The Efficacy of the Methanol Extract (LI12100) of *Annona squamosa* Comprising Acetogenins as Anti-Inflammatory and Anti-Cytokine Therapy The in vivo anti-inflammatory efficacy of *Annona squamosa* leaf methanol extract (LI12100; 0.24% squamocin C) was evaluated in Freund's Complete Adjuvant induced arthritis model of Sprague Dawley rats in comparison with positive control prednisolone. The rats of either sex were randomly selected and divided into four groups comprising 6 animals in each group. The treatment group rats were supplemented with 50 mg/kg body weight or 100 mg/kg body weight of *Annona squamosa* extract (LI12100) or 10 mg/kg body weight of prednisolone per day for 14 days. All the supplements were diluted in 10 mL of 1% CMC. The control group of animals was supplemented with same volume (10 mL) of 0.5% CMC. Prednisolone was administered as positive control. On the 14$^{th}$ day, Freund's Complete Adjuvant (FCA) was subcutaneously injected in the sub-plantar region of the left hind paw of each animal. The experiment was terminated 13 days after FCA inoculation. At the end of the experiment, the animals were sacrificed, the liver tissue samples excised and stored at −80° C. Blood samples were collected from each animal at regular intervals and paw volumes were measured on the day of FCA injection and after 13 days of FCA inoculation. The difference in paw edema volume at the day of FCA injection and at $13^{th}$ day after FCA inoculation is considered as the inflammatory response for the supplement. The in vivo anti-inflammatory responses of *Annona squamosa* extract (LI12100) and prednisolone were estimated by calculating the percentage inhibition of paw edema when compared to the paw edema observed in the CMC supplemented control group. The data is summarized in FIG. 5.

The treatment groups supplemented with 50 mg/kg body weight and 100 mg/kg body weight of *Annona squamosa* extract (LI12100) showed 49.5% and 64.5% reductions in paw volume respectively, when compared to the control group. The positive control group prednisolone showed 69.2% reduction in the paw edema. The levels of cytokine tumor necrosis factor-alpha (TNFα) were evaluated in blood serum collected 14 days after FCA challenge. The serum cytokine levels were measured using enzyme-immune assay kit supplied by R & D systems, USA. The treatment groups supplemented with LI12100 and prednisolone showed significant reduction in serum cytokine levels (TNFα) as depicted in FIG. 6.

Further, the levels of a wide range of cytokine biomarkers were estimated in the serum of the treatment groups and the control group using multiplex assay (RCYTOMAG 80K) following the instructions provided by the vendor (Millipore Corporation, Billerica, Mass., USA). The treatment groups supplemented with LI12100 significantly ameliorated the expression of many cytokines in the serum, when compared to their respective levels exhibited by control group. The cytokines ameliorated by LI12100 include TNFα, IFNγ, IL-1β, IL-2, IL-4, IL-6, IL-13, MCP-1, Rantes and Eotaxin as summarized in Table 3.

TABLE 3

Relative expressions of cytokines/chemokines related to inflammation in serum samples of FCA induced Sprague Dawley rats treated with LI12100 and prednisolone

| Cytokines/Chemokines | Relative expressions in | | | |
|---|---|---|---|---|
| | Vehicle control | LI 12100 (50 mg/kg) | LI 12100 (100 mg/kg) | Prednisolone (10 mg/kg) |
| TNFα | 1.000 | 0.732 | 0.654 | 0.754 |
| IFNγ | 1.000 | 1.112 | 1.142 | 1.496 |
| IL-1β | 1.000 | 0.845 | 0.693 | 0.848 |
| IL-2 | 1.000 | 0.556 | 0.501 | 0.515 |
| IL-4 | 1.000 | 0.716 | 0.662 | 0.831 |
| IL-6 | 1.000 | 0.750 | 0.694 | 1.377 |
| IL-13 | 1.000 | 2.343 | 3.306 | 3.120 |
| MCP-1 | 1.000 | 0.664 | 0.701 | 0.802 |
| Rantes | 1.000 | 0.797 | 0.605 | 0.874 |
| Eotaxin | 1.000 | 0.559 | 0.484 | 0.992 |

Rat Cytokine/chemokine Multiplex panel (Catalogue No. RCYTO-80K, Millipore Corporation, USA).

Example 18

Assessment of Inhibition of Lipid Accumulation in Differentiated Adipocytes by the Extracts and Fractions of *Annona squamosa*

One hundred thousand 3T3-L1 mouse pre-adipocyte cells in Dulbecco's Modified Eagle's Medium (DMEM) containing 10% Fetal Bovine Serum (FBS) were taken into each well of a 24-well plate and incubated for 24 h at 37° C. and 5% $CO_2$. Cells were pre-incubated with different concentrations of the ethyl acetate extract of *Annona squamosa* (LI12101) dissolved in 0.1% DMSO and then differentiated in a differentiation medium i.e. DMEM containing 500 nM insulin, 1.0 μM dexamethasone, and 0.5 mM isobutylmethylxanthine (IBMX) for 48 h. The cells incubated only with 0.1% DMSO were considered as the vehicle control. Thereafter, the differentiation medium was replaced by DMEM containing 100 nM insulin and cells in presence or absence of different concentrations of the extract LI12101 derived from *Annona squamosa* were incubated further for 8 days. After the treatment period, cells were fixed with 10% buffered formalin for 4 h at room temperature. The fixed cells were stained with Oil Red 0 solution (0.5 g in 100 ml isopropanol) for 10 min to measure the cellular neutral lipid accumulation. After removing the staining solution, the dye retained in the cells was eluted with isopropanol and OD was measured at 550 nm. The inhibition of fat accumulation in the treated cells was compared with the mock treated differentiated adipocytes. The anti-adipogenic activity of the *Annona squamosa* extract LI12101 is represented by percentage inhibition of lipid accumulation (Table 4).

The percentage inhibitions of lipid accumulation/adipogenesis caused by hexane extract (LI12100A), methanol extract (LI12100B), ethyl acetate extract (LI12100C) and ethanol extract (LI12100D) of *Annona squamosa* leaf were also determined using the similar protocol and data is summarized in the Table 4.

TABLE 4

Anti-adipogenic activities of the agents derived from *Annona squamosa*

| Name of the test product | Treatment concentration | % inhibition of adipogenesis |
|---|---|---|
| LI12101 | 10 μg/ml | 46.6 |
| LI12100A | 10 μg/ml | 37.2 |
| LI12100B | 10 μg/ml | 21.5 |
| LI12100C | 10 μg/ml | 43.3 |
| LI12100D | 10 μg/ml | 34.1 |
| | 25 μg/ml | 41.2 |

Example 19

Inhibition of Adipogenesis Markers PPARγ, ADRP, CD36, aP2, CEBPα, CEBPβ, Perilipin in 3T3-L1 Adipocytes by Methanol Extract of *Annona squamosa* (LI12100)

Mouse pre-adipocyte 3T3-L1 cells were maintained in Dulbecco's Modified Eagles Medium (DMEM) supplemented with 2 mM glutamine, 4.5 g/L glucose and 10% fetal bovine serum. Equal number of cells was plated in each well of 24-well culture plates. Cells were pre-treated separately with 5 and 10 μg/mL of LI12100 for 2 h and followed by addition of differentiation medium containing 500 nM insulin, 1.0 μM dexamethasone, and 0.5 mM isobutylmethylxanthine (IBMX) for 48 h. Thereafter, cells were further incubated with post differentiation medium (DMEM containing 100 nM insulin) in presence or absence of LI12100. Finally, the cells were harvested, washed with chilled phosphate buffered saline and lysed with the lysis buffer. The protein extracts were clarified at 14,000 g for 20 min. Protein content was measured in Bradford method by using Coomassie blue dye and cell lysates were stored in aliquots at −80° C. until further use. The modulation of adipocyte differentiation markers such as Peroxisome proliferator-activated receptor gamma (PPARγ), Adipose Differentiation Related Protein (ADRP), CEBPα, CEBPβ, CD36, adipocyte fatty acid binding protein (aP2); and intracellular lipid droplet surface associated protein, perilipin expression were evaluated by immunoblot assay.

Inhibition of protein expression of biomarker molecules in adipocytes in the presence or absence of LI12100 was evaluated in immunoblot assay. Briefly, equal amount of cell lysate proteins were resolved in 7.5% SDS-PAGE; thereafter, the proteins were transferred to nitrocellulose membrane. After blocking the non-specific sites, the membrane was incubated with either anti-PPARγ, or anti-CD36, or anti-aP2, or anti-ADRP, or anti-CEBPα or anti-CEBPβ or anti-perilipin antibody. Finally, the specific immuno-reactive bands were developed with West-pico chemiluminescent substrate (Pierce Biotechnology, Ill., USA), and the immunoblot images were recorded in a Kodak Image Station (Kodak, USA). Band intensities were calculated densitometrically and normalized with expression of actin in respective samples. The data is summarized in FIG. 1.

Example 20

Modulation of Adiponectin by LI12100

Modulation of adiponectin protein by LI12100 in 3T3-L1 adipocytes was evaluated in Western immunoblot assay. The cell culture, treatment protocol and immunoblot assay methodology were the same as described in Example 19. LI12100 dose dependently enhanced adiponectin protein expression in 3T3-L1 mature adipocytes. LI12100 at 5 μg/mL and 10 μg/mL showed 38% and 64% improvements in serum adiponectin concentration respectively.

We claim:

1. A solid oral dosage form for treatment of inflammation, comprising:
   an organic solvent extract of *Annona squamosa* in an amount effective for treatment of inflammation, said extract being prepared by a process comprising:
   a) pulverizing *Annona squamosa* seeds or *Annona squamosa* leaves;
   b) extracting said pulverized *Annona squamosa* seeds or *Annona squamosa* leaves with an organic solvent to obtain a solution;
   c) separating said solution from a spent raw material;
   d) concentrating said solution to obtain said organic solvent extract;
   wherein said solid oral dosage form is a tablet, soft capsule, hard capsule, soft gel capsule, pill, or a dosage form comprising a controlled release polymer-based coating;
   wherein said organic solvent extract is selected from the group consisting of:
      an alcoholic solvent extract of *Annona squamosa* leaves having an $IC_{50}$ for inhibition of TNFα of between about 20 and about 29 ng/ml;
      an ethyl acetate extract of *Annona squamosa* leaves;
      an ethyl acetate or hexane extract of *Annona squamosa* seeds; and
      a mixture thereof;
      with the proviso that if said organic solvent extract is a hexane extract of *Annona squamosa* seeds, said composition further comprises an effective amount of a second anti-inflammatory agent.

2. The solid oral dosage form according to claim 1, further comprising
   at least one component selected from the group consisting of vitamins, amino acids, minerals, and mixtures thereof.

3. The solid oral dosage form according to claim 1, further comprising:
   at least one extract or phytochemical having anti-inflammatory activity.

4. The solid oral dosage form according to claim 1, further comprising:
   at least one biologically active ingredient selected from the group consisting of:
      a compound selected from the group consisting of Glucosamine, Glucosamine salts, Chondroitin, Methylsulfonylmethane (MSM), Hyaluronic acid, collagen, polyglycans, Chitosan, Undenatured collagen type-II, SAM-e, NEM, quercetin, boron, manganese, ascorbic acid, ascorbic acid salts, flavonoids, alkaloids, phytosterols, terpenes, omega 3 fatty acids and mixtures thereof;
      an extract selected from the group consisting of an extract of *Withania somnifera*, an extract of *Sphaeranthus indices*, an extract of *Boswellia serrata*, an extract of *Curcuma longa*, an extract of *Psidium guajava*, an extract of pine bark, an extract of *Piper nigrum*, an extract of *Piper longum*, and mixtures thereof; and
   mixtures thereof.

5. The solid oral dosage form according to claim 1, herein the percentage of said extract of *Annona squamosa* in the dosage form is between about 0.01% and about 99.9% by weight.

6. The solid oral dosage form according to claim 5, wherein the percentage of said extract of *Annona squamosa* in the dosage form is between about 0.1% and about 50% by weight.

7. The solid oral dosage form according to claim 1, further comprising at least one dietetically acceptable inactive ingredient is selected from the group consisting of surfactants, binders, disintegrants, lubricants, preservatives, stabilizers, buffers, suspensions, drug delivery systems, and mixtures thereof.

8. The solid oral dosage form according to claim 1, wherein said at least one dietetically acceptable inactive ingredient is selected from the group consisting of glucose, fructose, sucrose, maltose, lactose, yellow dextrin, white dextrin, silicon dioxide, microcrystalline cellulose powder, calcium stearate, magnesium stearate, sorbitol, stevioside, corn syrup, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, nicotinamide, calcium pantothenate, calcium salts, pigments, flavors, preservatives, distilled water, saline, aqueous glucose solution, alcohol, propylene glycol and polyethylene glycol, animal and vegetable oils, white soft paraffin, paraffin, wax, and mixtures thereof.

9. The solid oral dosage form of claim 1, wherein said process further comprises:
   e) extracting the spent raw material with water to obtain a second solution;
   f) separating said second solution from the spent raw material;
   g) concentrating said second solution to obtain a water extract; and
   h) mixing said organic solvent extract and said water extract.

10. A method of modulating the expression or production of at least one cytokine, chemokine or a biological marker selected from the group consisting of TNFα, IL-1β, IL-2, IL-4, IL-6, IL-13, MCP-1, aP2, Rantes, Eotaxin, FLAP, ICAM, VCAM and MMPs in mammal in need thereof,
   wherein the method comprises supplementing said mammal with an effective dose of a solid oral dosage form according to claim 1.

11. A method of controlling or treating obesity,
wherein the method comprises supplementing said mammal with an effective dose of a solid oral dosage form according to claim 1.

12. A method of modulating the expression or production of at least one biological marker selected from PPAR-γ, C-reactive protein (CRP), Adipose Differentiation Related Protein (ADRP), CCAAT/enhancer-binding protein alpha (CEBPα), CCAAT/enhancer-binding protein beta (CEBPβ), adipocyte CD36, macrophage CD36, Monocyte Chemotactic protein (MCP-1), Oxidized LDL, Adipocyte Fatty-acid-Binding Protein (aP2/FABP4/A-FABP), Beta-3 adrenergic receptor (β3-AR), adiponectin, Perilipin, Protein tyrosine phosphatase 1B (PTP 1B), Matrix Metalloproteinase-1 (MMP-1), Matrix Metalloproteinase-3 (MMP-3) and Matrix Metalloproteinase-13 (MMP-13) in a mammal in need thereof,
wherein the method comprises supplementing said mammal with an effective dose of a solid oral dosage form according to claim 1.

13. A method of treating inflammation in a mammal,
wherein the method comprises supplementing the said mammal with an effective dose of a solid oral dosage form according to claim 1.

14. The method according to claim 13, wherein said solid oral dosage form further comprises:
at least one biologically active ingredient selected from the group consisting of:
a compound selected from the group consisting of Glucosamine, Glucosamine salts, Chondroitin, Methylsulfonylmethane (MSM), Hyaluronic acid, collagen, polyglycans, Chitosan, Undenatured collagen type-II, SAM-e, NEM, quercetin, boron, manganese, ascorbic acid, ascorbic acid salts, flavonoids, alkaloids, phytosterols, terpenes, omega 3 fatty acids and mixtures thereof;
an extract selected from the group consisting of an extract of *Withania somnifera*, an extract of *Sphaeranthus indices*, an extract of *Boswellia serrata*, an extract of *Curcuma longa*, an extract of *Psidium guajava*, an extract of pine bark, an extract of *Piper nigrum*, an extract of *Piper longum*, and mixtures thereof; and mixtures thereof.

15. A solid oral dosage form for treatment of inflammation, made by:
1) providing an ethyl acetate extract of *Annona squamosa* leaves, said ethyl acetate extract being prepared by a process comprising:
a) pulverizing said *Annona squamosa* leaves;
b) extracting said pulverized *Annona squamosa* leaves with hexane to obtain a first solution;
c) separating said first solution from a spent raw material;
d) extracting said spent raw material with ethyl acetate to obtain a second solution;
e) concentrating said second solution to obtain said ethyl acetate extract; and
2) incorporating an effective amount of said extract into a solid oral dosage form.

16. A solid oral dosage form for treatment of inflammation, comprising;
i) an organic solvent extract of *Annona squamosa* seeds in an amount effective for treatment of inflammation, said organic solvent extract comprising acetogenins and being prepared by a process comprising:
a) pulverizing said *Annona squamosa* seeds;
b) extracting said pulverized *Annona squamosa* seeds with ethyl acetate or hexane to obtain a solution;
c) separating said solution from a spent raw material;
d) concentrating said solution to obtain said organic solvent extract; and
ii) a second anti-inflammatory agent which is an organic solvent extract of *Annona squamosa* leaves or an anti-inflammatory extract of a plant other than *Annona squamosa*;
wherein said solid oral dosage form is a tablet, soft capsule, hard capsule, soft gel capsule, pill, or a dosage form comprising a controlled release polymer-based coating.

17. The dosage form according to claim 16, wherein said a solid oral dosage form comprises a controlled release tablet, said controlled release tablet comprising:
a core containing said at least one compound selected from the group consisting of acetogenins; and
a controlled release polymer-based coating.

18. A solid oral dosage form for treatment of inflammation, comprising:
i) an organic solvent extract of *Annona squamosa* leaves in an amount effective for treatment of inflammation, said organic solvent extract comprising acetogenins and being prepared by a process comprising:
a) pulverizing said *Annona squamosa* leaves;
b) extracting said pulverized *Annona squamosa* leaves with alcohol or ethyl acetate to obtain a solution;
c) separating said solution from a spent raw material;
d) concentrating said solution to obtain said organic solvent extract; and
ii) a second anti-inflammatory agent which is an ethyl acetate or hexane extract of *Annona squamosa* leaves or an anti-inflammatory extract of a plant other than *Annona squamosa*;
wherein said solid oral dosage form is a tablet, soft capsule, hard capsule, soft gel capsule, pill, or a dosage form comprising a controlled release polymer-based coating.

19. A solid oral dosage form for treatment of inflammation, comprising:
an organic solvent extract of *Annona squamosa* in an amount effective for treatment of inflammation, said extract being prepared by a process comprising:
a) pulverizing *Annona squamosa* seeds or *Annona squamosa* leaves;
b) extracting said pulverized *Annona squamosa* seeds or *Annona squamosa* leaves with an organic solvent to obtain a solution;
c) separating said solution from a spent raw material;
d) concentrating said solution to obtain said organic solvent extract;
wherein said solid oral dosage form is a tablet, soft capsule, hard capsule, soft gel capsule, pill, or a dosage form comprising a controlled release polymer-based coating;
wherein said organic solvent extract is selected from the group consisting of:
an organic solvent extract of *Annona squamosa* leaves having an $IC_{50}$ for inhibition of TNFα of between about 8 and about 29 ng/ml;
an ethyl acetate extract of *Annona squamosa* seeds;
and
a mixture thereof.

* * * * *